US009617499B2

(12) United States Patent
Jeon et al.

(10) Patent No.: US 9,617,499 B2
(45) Date of Patent: *Apr. 11, 2017

(54) METHOD OF PRODUCING ESTOLIDE USING LINKING AGENT

(71) Applicants: SK INNOVATION CO., LTD., Seoul (KR); SK LUBRICANTS CO., LTD., Seoul (KR)

(72) Inventors: Hee Jung Jeon, Daejeon (KR); Jong Su Lee, Gwangju (KR); Yong Woo Kim, Daejeon (KR)

(73) Assignees: SK INNOVATION CO., LTD., Seoul (KR); SK LUBRICANTS CO., LTD., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/887,714

(22) Filed: Oct. 20, 2015

(65) Prior Publication Data
US 2016/0108343 A1 Apr. 21, 2016

(30) Foreign Application Priority Data

Oct. 21, 2014 (KR) ......................... 10-2014-0142873

(51) Int. Cl.
*C11C 3/00* (2006.01)
*C10M 105/34* (2006.01)
(Continued)

(52) U.S. Cl.
CPC ............. *C11C 3/003* (2013.01); *C07C 51/09* (2013.01); *C07C 51/36* (2013.01); *C07C 51/44* (2013.01);
(Continued)

(58) Field of Classification Search
CPC . C11C 1/00; C11C 1/005; C11C 3/003; C11C 3/12; C11B 7/00; C07C 67/333; C10M 105/36; C10M 177/00
See application file for complete search history.

(56) References Cited

U.S. PATENT DOCUMENTS 6,018,063 A 1/2000 Isbell et al.
9,018,406 B2 † 4/2015 Forest
(Continued)

FOREIGN PATENT DOCUMENTS

EP 057224 A1 9/1992
WO 99/25794 A1 5/1999
WO 2011/037778 A1 3/2011

OTHER PUBLICATIONS

Witte, P. et al., Water solubility, antioxidant activity and cytochrome C binding of four families of exohedral adducts of C60 and C70, 2007, Org. Biomol. Chem., vol. 5 pp. 3599-3613.*
(Continued)

*Primary Examiner* — Yate K Cutliff
(74) *Attorney, Agent, or Firm* — Abelman, Frayne & Schwab

(57) ABSTRACT

Disclosed is a method of producing an estolide, including a) converting biomass-derived oil into a fatty acid mixture, b) separating the fatty acid mixture into a C16 saturated fatty acid and a C18 unsaturated fatty acid, c) converting the C16 saturated fatty acid into a C15 or C16 linear internal olefin, d) subjecting the C15 or C16 linear internal olefin to an estolide reaction using a linking agent, thus obtaining an estolide A, e) subjecting the C18 unsaturated fatty acid to partial hydrogenating to increase the amount of oleic acid, and f) subjecting the oleic acid to an estolide reaction using a linking agent and then esterification, thus obtaining an estolide B.

20 Claims, 5 Drawing Sheets

(51) Int. Cl.
| | |
|---|---|
| *C11C 3/12* | (2006.01) |
| *C10M 105/36* | (2006.01) |
| *C07C 67/333* | (2006.01) |
| *C10M 177/00* | (2006.01) |
| *C11B 7/00* | (2006.01) |
| *C07C 67/04* | (2006.01) |
| *C07C 67/08* | (2006.01) |
| *C07C 69/24* | (2006.01) |
| *C07C 69/40* | (2006.01) |
| *C07C 69/50* | (2006.01) |
| *C07C 69/67* | (2006.01) |
| *C07C 51/09* | (2006.01) |
| *C07C 51/36* | (2006.01) |
| *C07C 51/44* | (2006.01) |
| *C11C 1/00* | (2006.01) |

(52) U.S. Cl.
CPC .............. *C07C 67/04* (2013.01); *C07C 67/08* (2013.01); *C07C 67/333* (2013.01); *C07C 69/24* (2013.01); *C07C 69/40* (2013.01); *C07C 69/50* (2013.01); *C07C 69/67* (2013.01); *C10M 105/34* (2013.01); *C10M 105/36* (2013.01); *C10M 177/00* (2013.01); *C11B 7/00* (2013.01); *C11C 1/005* (2013.01); *C11C 3/12* (2013.01); *C11C 1/00* (2013.01)

(56) References Cited

U.S. PATENT DOCUMENTS

| | | | | |
|---|---|---|---|---|
| 2012/0322897 | A1* | 12/2012 | Bredsguard | C10M 169/04 514/785 |
| 2013/0085090 | A1* | 4/2013 | Kim | H02K 5/1675 508/404 |
| 2013/0261325 | A1* | 10/2013 | Forest | C10M 105/42 554/122 |
| 2014/0018270 | A1* | 1/2014 | Kim | C10M 141/10 508/409 |

OTHER PUBLICATIONS

Purdy, R.E., Hydrolysis of plant cuticle by plant pathogens, Properties of Cutinase I, Cutinase II, and a nonspecific esterase, 1975, Biochemistry, vol. 14, No. 13, pp. 2832-2840.*
Harry-O kuru, R. et al., Synehsis of estolide esters from cis-9-octadecenoic acid estolides, 2001, JAOCA, vol. 78, No. 3, pp. 219-223.*
Isbell, et al., "Physical Properties of Triglyceride Estolides from Lesquerella and Castor Oils," Industrial Crops and Products, 23(3): 256-263 (2006).

* cited by examiner
† cited by third party

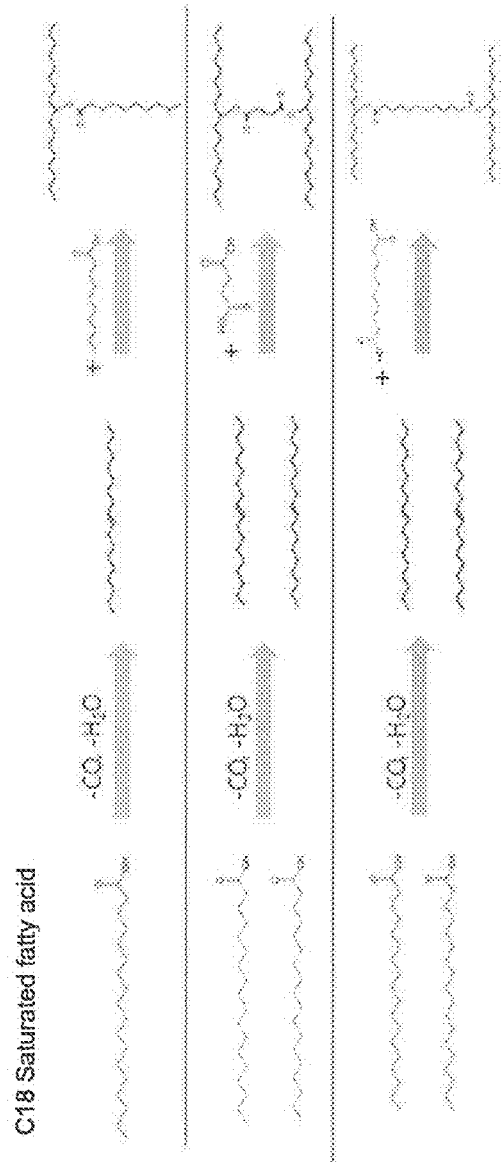

METHOD OF PRODUCING ESTOLIDE USING LINKING AGENT

CROSS-REFERENCE TO RELATED APPLICATION

This application claims the benefit of Korean Patent Application No. 10-2014-0142873, filed Oct. 21, 2014, entitled "A method of producing estolides using a linking agent", which is hereby incorporated by reference in its entirety into this application.

BACKGROUND OF THE INVENTION

1. Technical Field

The present invention relates to a method of producing novel estolides, in which the advantageous properties of existing estolides are retained and the shortcomings thereof are overcome and, more particularly, to a method of producing estolides using a linking agent.

2. Description of the Related Art

Petroleum resources, which significantly contribute to the pollution of the global environment, are strictly regulated at refineries. Moreover, petroleum resources obtained by raising S, N, heavy metals, aromatics, etc. up to the earth's surface from deep underground are refined to thereby produce lubricants, but such lubricants have low biodegradability. When introduced to ecosystems, such lubricants have great influences on biological circulation systems, and problems of ecological disturbance caused by chemicals may occur in the real world. Furthermore, direct crude oil spills, chemical spills, and silent oil spills may take place, causing problems for ecosystems.

Thus, efforts to replace petroleum resources with environmentally friendly alternatives are being made. A representative material thereof is biomass-derived oil.

Biomass-derived oil is a primary product obtained by squeezing fruits obtained through planting and cultivating trees. Since carbon from such biomass-derived oil comes from $CO_2$ that is already in the atmosphere of the earth, unlike mineral oil, which is derived from fossil carbon, there is no additional generation of $CO_2$ in the atmosphere of the earth, and the $CO_2$ concentration in the atmosphere may in fact decrease, thus contributing to total $CO_2$ reduction through environmental rehabilitation. Consequently, the use of biomass-derived oil positively affects environmental rehabilitation, and may contribute to total $CO_2$ reduction through environmental rehabilitation, thereby allowing for the additional use of fossil carbon.

Although diesel has been used as a drilling fluid, at present only 100% environmentally friendly chemicals are permitted to be utilized based on legal regulations due to awareness of such environmental issues. As for diesel, biomass-derived environmentally friendly diesel is regulated to be compulsorily used in amounts less than 10% in most of the world, and the proportion thereof is gradually increasing.

As for lubricating oil, legal regulations for the use of environmentally friendly lubricating oil have not yet been introduced. Although ester lube has been introduced as an environmentally friendly lubricating oil, it is a chemical and is thus about four times as expensive as crude oil-based lubricating oil, and the amount thereof that can be produced is limited, making it impossible to produce the amounts required by markets. However, there is already consensus that currently useful lubricating oil is an environmental pollutant. Lubricating oil resulting from crude oil is known to have biodegradability of 10 to 30% on the basis of CEC analysis, and 1 liter of lubricating oil prepared from crude oil is already regarded as an environmental pollutant that pollutes 1 million liters of water. However, as techniques for manufacturing biomass-derived lubricating oil have been recently devised, the use of environmentally friendly lubricating oil has come to the fore. For example, regulations governing the use of environmentally friendly oil at places adjacent to oceans, rivers and the like were passed in December 2013 in the USA, and a bill (California senate bill 916) stipulating that 25% of gasoline and diesel engine oil be replaced with environmentally friendly lubricating oil by 2017 has been proposed in California. Although the bill in California failed to be established due to the high cost of manufacturing environmentally friendly lubricating oil, the fundamental purport thereof resonates with most people, and there is a continuous need for the use of environmentally friendly lubricating oil.

In order to manufacture environmentally friendly lubricating oil having high biodegradability and containing no toxic materials (S, N, aromatics, heavy metals), methods of using biomass may be readily taken into consideration. Since biomass is an environmentally friendly material having a very high biodegradability of about 70 to 100% and does not contain toxic materials such as S, N, aromatics and heavy metals, when lubricating oil is manufactured using biomass, environmentally friendly lubricating oil as described above may be expected to result. Also, petroleum resources are problematic because $CO_2$, which is a greenhouse gas, is added to the earth's circulation system, whereas biomass is a hydrocarbon that is already present in the biosphere. Hence, the additional conversion of biomass into lubricating oil means that the hydrocarbons of biomass are simply converted into lubricating oil in terms of the earth's overall circulation system, advantageously preventing the additional generation of $CO_2$ in the earth's circulation system. The existing biomass industry has problems such as the generation of only small amounts of biomass and the requirement to collect biomass, but biomass commercialization markets are becoming very large, and thus crude palm oil (CPO), soy bean oil (SBO) and the like may be traded in amounts of at least 1 million tons on open markets in Singapore and Indonesia. Furthermore, byproducts such as free fatty acids may be purchased in amounts of hundreds of thousands of tons on open markets, and may then be made into products, thus eliminating problems regarding the amounts and collection of materials.

These days, estolide is receiving great attention as a biomass-derived environmentally friendly lubricating oil. If bill 916 of California had been actually established, estolide was intended to be used as an environmentally friendly lubricating oil. The term 'estolide' refers to any material in which unsaturated double bonds of hydrocarbons are cross-linked with a carboxylic acid functional group. Estolide, which is naturally present in castor- or *Lesquerella*-derived vegetable oil, was noted as being simply synthesized by Penoyer et al in 1954, and thus shows promise as a novel product.

The applicability of estolide as lubricating oil (Group V, ester base oil) was initially recognized due to the structural properties thereof. For example, triglyceride-derived estolide, which was prepared in the beginning, exhibits a good pour point (PP 9 to −36° C.) but has poor oxidation stability (RPVOT 29 to 52 min), and thus cannot be directly used as lubricating oil. As techniques have been devised for improving oxidation stability using oleic acid as an estolide feed through partial hydrogenating by use of an additive, the applicability thereof to high-quality lubricating base oil and cosmetic materials is significantly increasing.

The conventional process for producing estolide includes four steps, namely de-esterification, estolide synthesis, esterification, and hydrogenation. De-esterification is a step of converting triglycerides, which constitute most biomass-derived oil, into fatty acids, estolide synthesis is a step of converting unsaturated fatty acids into estolides, esterification is a step of converting the carboxylic acid functional group of an estolide into ester through a reaction with alcohol so as to stabilize it, and hydrogenation is a step of eliminating unsaturated double bonds from an estolide to thereby increase oxidation stability.

The estolide thus produced manifests the characteristics of a high-quality lubricating base oil having high viscosity index, superior oxidation stability and high thermal stability, compared to conventional petroleum-based Group I, Group II, and Group III base oil products. Estolides are considerably favorable in terms of making lubricating base oil having high viscosity based on 100 vis.

However, conventional methods of producing estolides have the following problems.

The first problem is the dependence on oleic acid. Early estolide research was ongoing into the direct preparation of estolides from triglycerides for use as lubricating base oil. However, in the case where a triglyceride is directly used, low-temperature stability may become problematic, and thus the resulting oil is unsuitable for use as lubricating base oil. Hence, as oleic acid is selectively used to produce estolides, the problem of low-temperature stability may be significantly alleviated, and the properties may be enhanced. In other words, the dependence on oleic acid is very high when producing estolides. However, the amount of oleic acid that can be derived from biomass is limited. Table 1 below shows the hydrocarbon chains that constitute the triglycerides of CPO and SBO, which are commercially applicable. As is apparent from Table 1, oleic acid comprises about 52 wt % of palm oil. The remaining materials other than oleic acid are not contained in estolides, and are thus not used. Only the amount of biomass-derived oil corresponding to oleic acid may be used, which is merely 50 wt % at most. The remaining fatty acids other than oleic acid are disadvantageous in that there is no end use therefor.

TABLE 1

| Fatty acid | Soy Bean Oil | Palm Oil |
|---|---|---|
| 12:0 Lauric acid | | <1.2 |
| 14:0 Myristic acid | 0.4 | 0.5 to 5.9 |
| 14:1 Myristoleic acid | | |
| 16:0 Palmitic acid | 7 to 14 | 32 to 59 |
| 16:1 Palmitoleic acid | <0.5 | <0.6 |
| 18:0 Stearic acid | 1.4 to 5.5 | 1.5 to 8.0 |
| 18:1 Oleic acid | 19 to 30 | 27 to 52 |
| 18:2 Linoleic acid | 44 to 62 | 5.0 to 14 |
| 18:3 Linolenic acid | 4.0 to 11 | <1.5 |
| 20:0 Eicosanoic acid | <1.0 | <1.0 |
| 22:0 Docosanoic acid | <1.0 | |

Second, hydrotreating is essentially required. In conventional estolide production reactions, hydrofinishing is performed in order to remove unsaturated double bonds from biomass-derived oil. Since oxidation stability is decreased in the presence of unsaturated double bonds, such unsaturated double bonds must be essentially removed through hydrogenation. In the conventional estolide reaction, unsaturated double bonds of estolides are eliminated through hydrogenation, especially hydrofinishing. However, hydrogenation is problematic because it requires reaction conditions of high temperature and high pressure and also because the price of hydrogen is very high, undesirably negating economic benefits. Hence, the production of estolides without conducting hydrogenation is regarded as very desirable.

Third, unsaturated double bonds may remain in estolides, despite the reaction for removing unsaturated double bonds using such hydrogenation. In the case where lubricating oil has unsaturated double bonds in the molecular structure thereof, there may occur side reactions, including discoloration through the coupling of unsaturated double bonds and oxygen in air, and the high likelihood of corrosion due to high bindability with moisture in the air. Accordingly, it is important that unsaturated double bonds be completely removed through hydrogenation so that no unsaturated double bonds remain. For estolides, some ester bonds may break in the course of the reaction for completely removing unsaturated double bonds, and thus the selective removal of unsaturated double bonds is carried out under the condition that ester bonding is maintained. For this reason, it is difficult to completely remove unsaturated double bonds. Unsaturated double bonds may be left behind at a level corresponding to an iodine value of less than 10.

SUMMARY OF THE INVENTION

Accordingly, the present invention has been made keeping in mind the problems encountered in the related art, and an aspect of the present invention is to provide a novel method of producing estolides from biomass-derived oil that is present in nature.

In addition, an aspect of the present invention is to provide a method of producing an estolide compound, in which the remaining fatty acids other than oleic acid, among the kinds of biomass-derived fatty acids, may be converted into linear internal olefin (LIO), thus generating economic benefits.

In addition, an aspect of the present invention is to provide a method of producing an estolide compound, in which the amount of oleic acid may be increased, thus minimizing the dependence on oleic acid in the course of forming the estolide compound, thereby improving profitability.

In addition, an aspect of the present invention is to provide a novel estolide and a lubricating oil including the same.

An embodiment of the present invention provides a method of producing an estolide, comprising: a) converting biomass-derived oil into a fatty acid mixture; b) separating the fatty acid mixture into a C16 saturated fatty acid and a C18 unsaturated fatty acid; c) converting the C16 saturated fatty acid into a C15 or C16 linear internal olefin; d) subjecting the C15 or C16 linear internal olefin to an estolide reaction using a linking agent, thus obtaining an estolide A; e) subjecting the C18 unsaturated fatty acid to partial hydrogenating to increase the amount of oleic acid; and f) subjecting the oleic acid to an estolide reaction using a linking agent and then esterification, thus obtaining an estolide B.

In an embodiment of the present invention, the linking agent may be dicarboxylic acid, tricarboxylic acid, or polycarboxylic acid, and the linking agent may be linear dicarboxylic acid or branched dicarboxylic acid. Furthermore, the linking agent may be oxalic acid, malonic acid, succinic acid, glutaric acid, adipic acid, pimelic acid, suberic acid, azelaic acid, sebacic acid, or 1-decanoic acid.

In an embodiment of the present invention, the subjecting the C18 unsaturated fatty acid to partial hydrogenating may comprise converting linoleic acid or linolenic acid into oleic acid.

In an embodiment of the present invention, the converting the C16 saturated fatty acid into the C15 linear internal olefin may be performed using decarbonylation, and the converting the C16 saturated fatty acid into the C16 linear internal olefin may be performed using partial hydrogenating for converting the C16 saturated fatty acid into a fatty alcohol and dehydration.

In an embodiment of the present invention, b) may further comprise g) separating a C18 saturated fatty acid.

In an embodiment of the present invention, the method may further comprise h) converting the C18 saturated fatty acid into a C17 or C18 linear internal olefin; and i) subjecting the C17 or C18 linear internal olefin to an estolide reaction using a linking agent, thus obtaining an estolide C.

In an embodiment of the present invention, a) may be performed by subjecting triglyceride in the biomass-derived oil to de-esterification or hydrolysis.

In an embodiment of the present invention, the method may further comprise j) separating or purifying the estolide A, and k) recirculating a linear internal olefin or mono-substituted estolide separated or purified in j) back to d).

In an embodiment of the present invention, the method may further comprise l) separating or purifying the estolide B after f), or separating or purifying the estolide produced after the estolide reaction in f), and m) recirculating a C18 fatty acid or mono-substituted estolide separated or purified in l) back to f).

Another embodiment of the present invention provides an estolide, produced by the method according to an embodiment of the present invention. The estolide may be used as a lubricating oil.

A further embodiment of the present invention provides an estolide, comprising at least one selected from the group consisting of an estolide A, configured such that a carboxylic acid functional group of a linking agent is linked to a position of a double bond in a C15 or C16 linear internal olefin; an estolide B in ester form, configured such that a carboxylic acid functional group of a linking agent is linked to a position of a double bond in oleic acid; and an estolide C, configured such that a carboxylic acid functional group of a linking agent is linked to a position of a double bond in a C17 or C18 linear internal olefin. The linking agent may be dicarboxylic acid, tricarboxylic acid, or polycarboxylic acid, and particularly, may be linear dicarboxylic acid or branched dicarboxylic acid. More particularly, the linking agent may be oxalic acid, malonic acid, succinic acid, glutaric acid, adipic acid, pimelic acid, suberic acid, azelaic acid, sebacic acid, or 1-decanoic acid.

The estolide may be represented by Chemical Formulas 1 to 15 below:

[Chemical Formula 1]
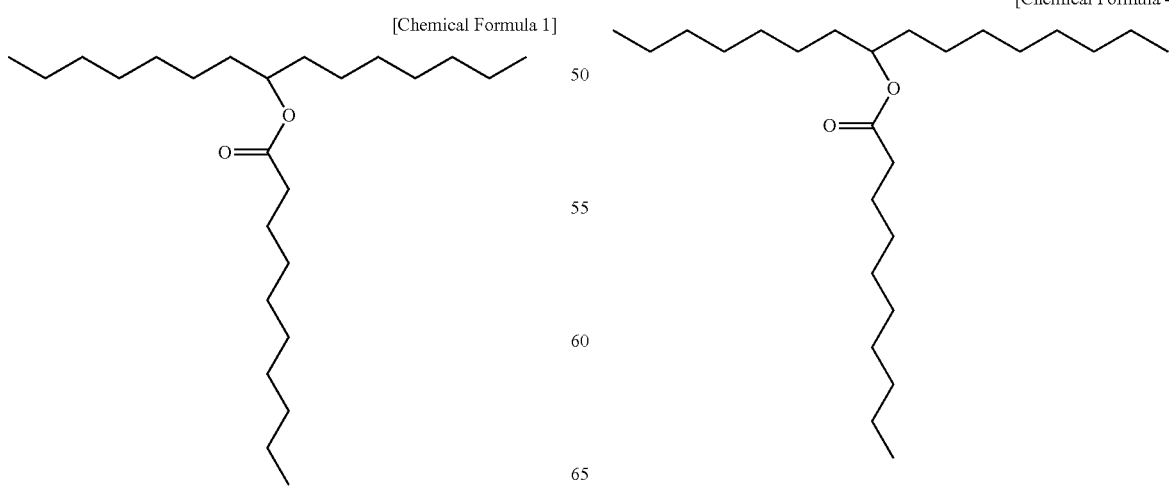

[Chemical Formula 2]
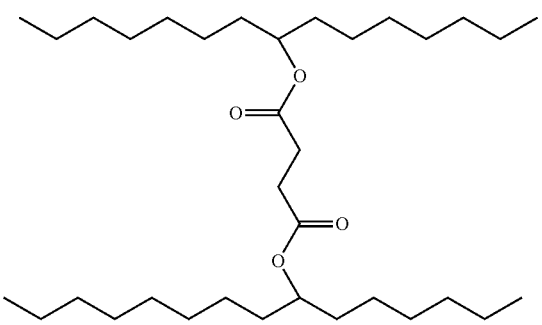

[Chemical Formula 3]
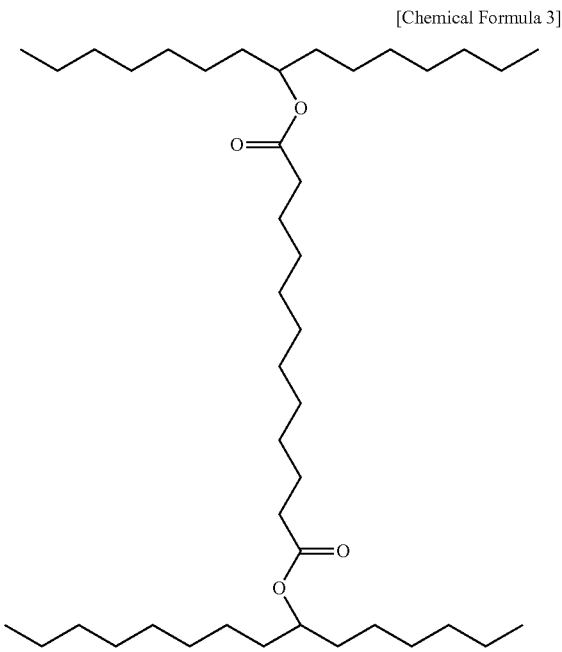

[Chemical Formula 4]

[Chemical Formula 5]
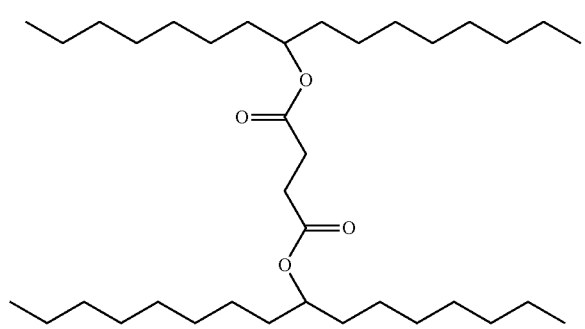
[Chemical Formula 6]
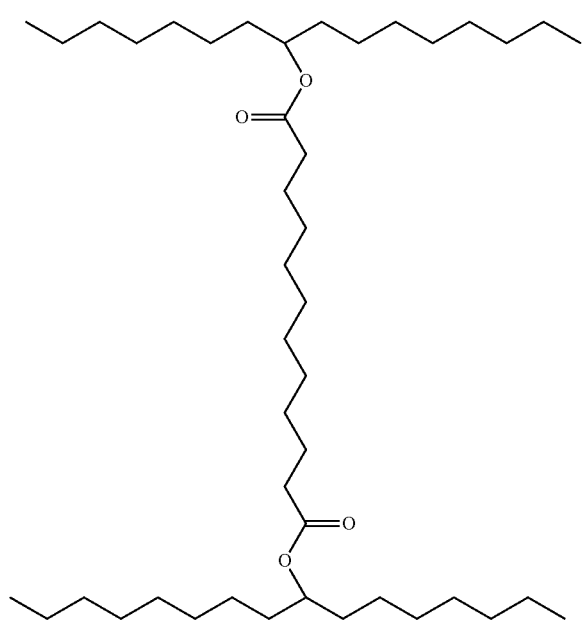
[Chemical Formula 7]
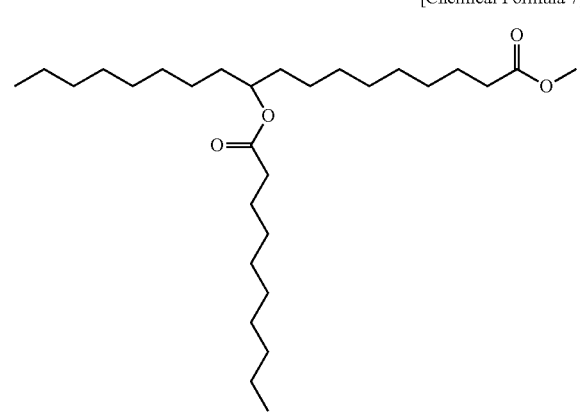
[Chemical Formula 8]
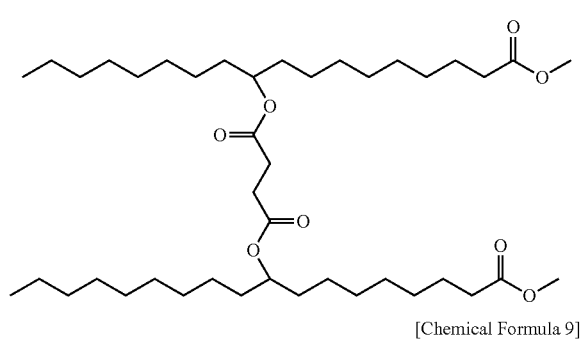
[Chemical Formula 9]
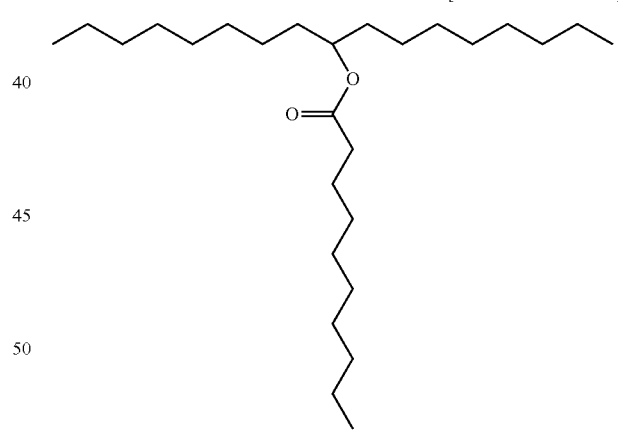
[Chemical Formula 10]
[Chemical Formula 11]
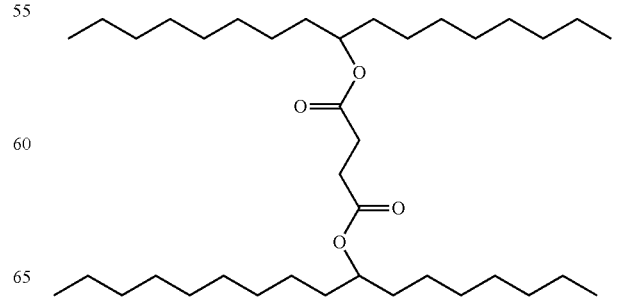

[Chemical Formula 12]

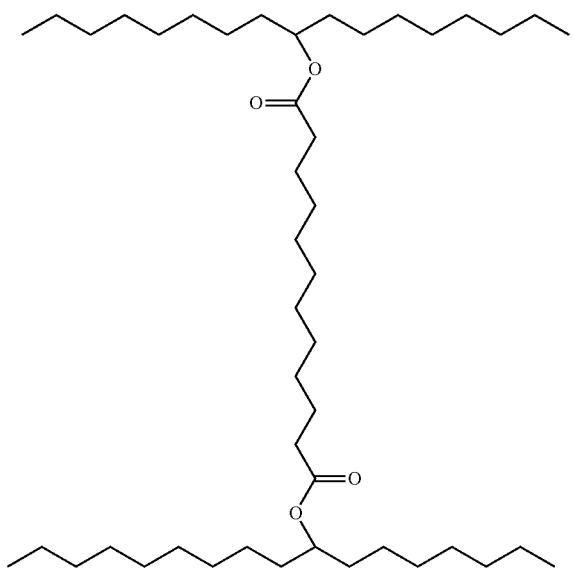

[Chemical Formula 13]

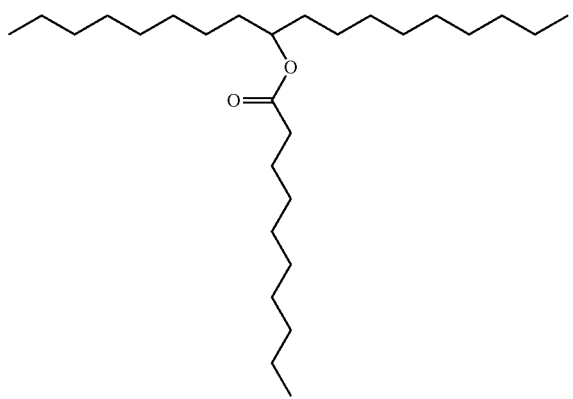

[Chemical Formula 14]

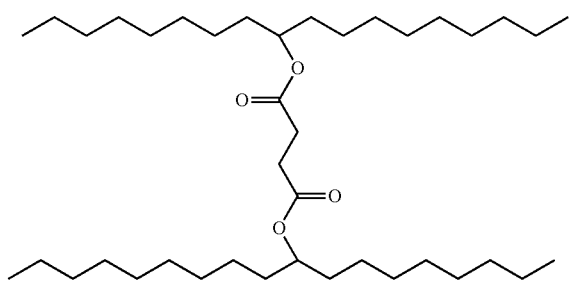

[Chemical Formula 15]

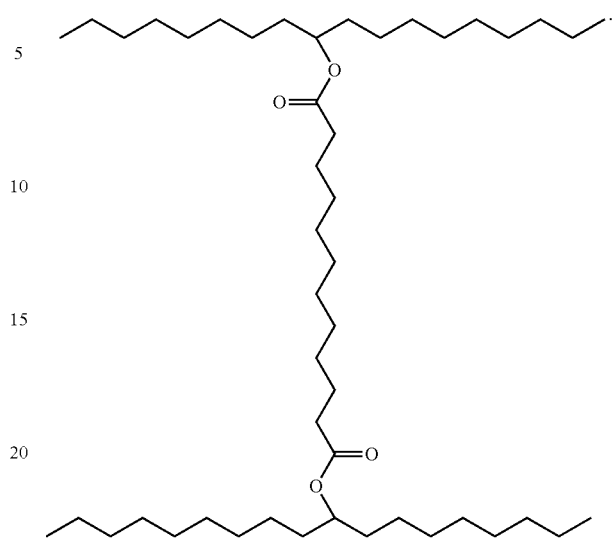

According to an aspect of the present invention, produced estolides have no residual unsaturated double bonds, unlike existing estolide products, and also contain an ester functional group having high steric hindrance in the molecules thereof, and are thus advantageous because it is difficult to convert the ester into an acid. Furthermore, the produced materials can be used in combination, thereby manufacturing environmentally friendly lubricating base oil products that exhibit properties similar to those of conventional PAO lubricating oil.

Also, produced estolides can realize the advantages of environmentally friendly lubricating oil. Examples of the advantages of lubricating oil that estolides can retain include high biodegradability, a high viscosity index, good low-temperature stability, etc.

According to another aspect of the present invention, a method of producing estolides enables a C18 unsaturated fatty acid to undergo partial hydrogenating, thereby producing oleic acid in a large amount, compared to conventional estolide production processes, and is thus considerably technically competitive and obviates the need for hydrofinishing. Furthermore, although only oleic acid is used in conventional estolide production processes, fatty acids other than oleic acid can be utilized in the present invention, whereby there are no remaining fatty acid byproducts, ultimately obviating the need for additional treatment. Moreover, estolides having various properties can be produced depending on the kind of linking agent according to the present invention.

BRIEF DESCRIPTION OF THE DRAWINGS

FIG. 2c illustrates the reaction mechanisms for producing estolides from C18 saturated fatty acid according to an aspect of the present invention.

DESCRIPTION OF SPECIFIC EMBODIMENTS

Hereinafter, embodiments of the present invention are described in detail. Such embodiments are merely illustrative, and are not to be construed as limiting the present invention.

Figure 1:
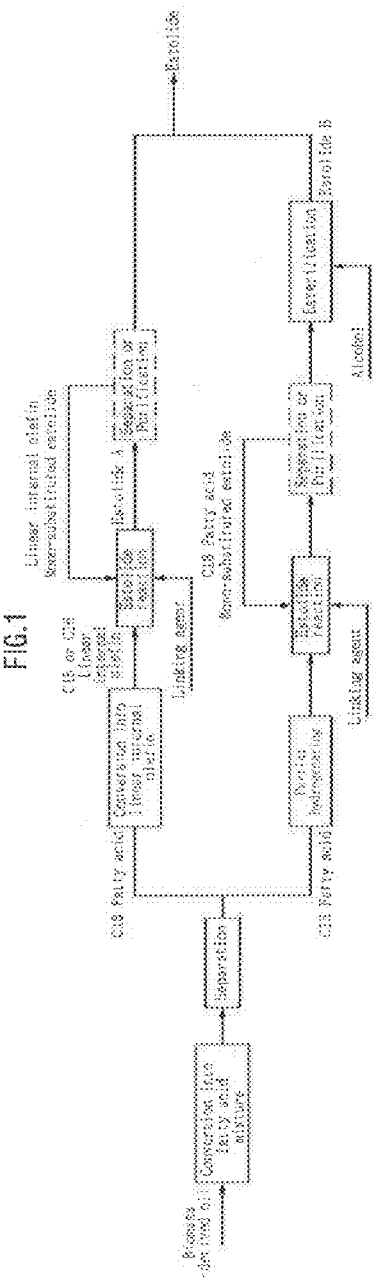
FIG. 1 schematically illustrates the process of producing novel estolides according to an aspect of the present invention.

With reference to FIG. 1, biomass-derived oil is converted into a fatty acid mixture, after which the fatty acid mixture is separated into a C16 saturated fatty acid and a C18 unsaturated fatty acid. Further, the separated C16 saturated fatty acid is converted into a C15 or C16 linear internal olefin (LIO) through an LIO conversion process, and then the C15 or C16 linear internal olefin is subjected to an estolide reaction using a linking agent, thus obtaining an estolide A. As necessary, separating or purifying the estolide A may be further performed, and the separated linear internal olefin and mono-substituted estolide may be recirculated back to the estolide reaction step. The C18 unsaturated fatty acid is subjected to partial hydrogenating to increase the amount of oleic acid, and the oleic acid thus obtained is subjected to an estolide reaction using a linking agent and then esterification, thus obtaining an estolide B. As necessary, separation or purification may be performed, either after the estolide reaction of oleic acid or after esterification. The separated C18 fatty acid or mono-substituted estolide may be recirculated back to the estolide reaction step. The estolides thus obtained may be used alone or in combination, resulting in a final estolide product.

Figure 2A:
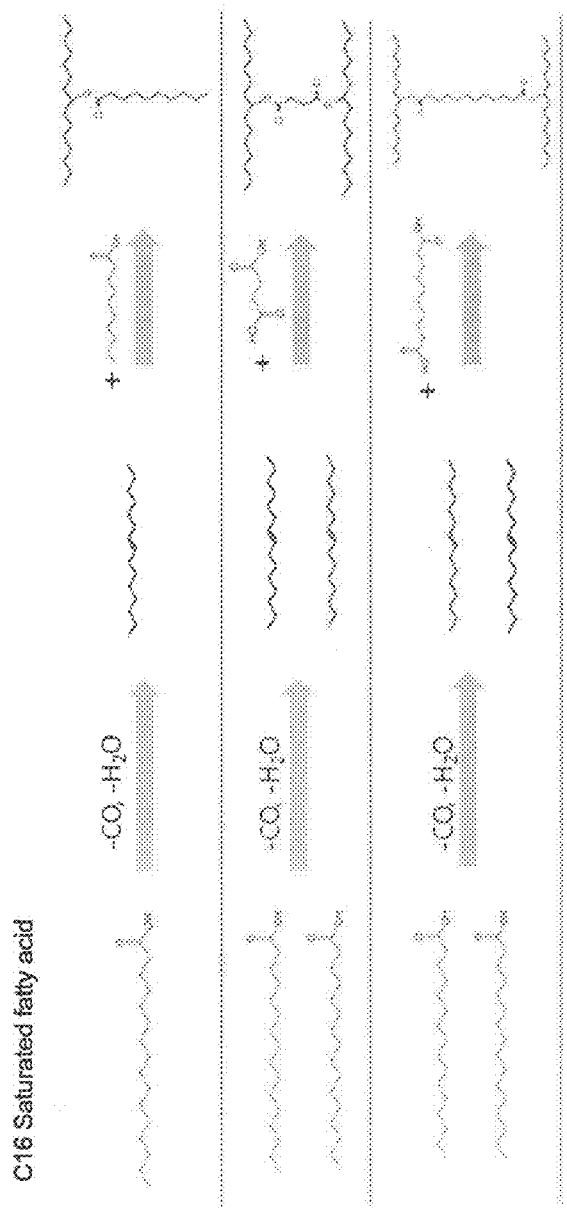
FIG. 2a illustrates the reaction mechanisms for producing estolides from C16 saturated fatty acid according to an aspect of the present invention.
Figure 2B:
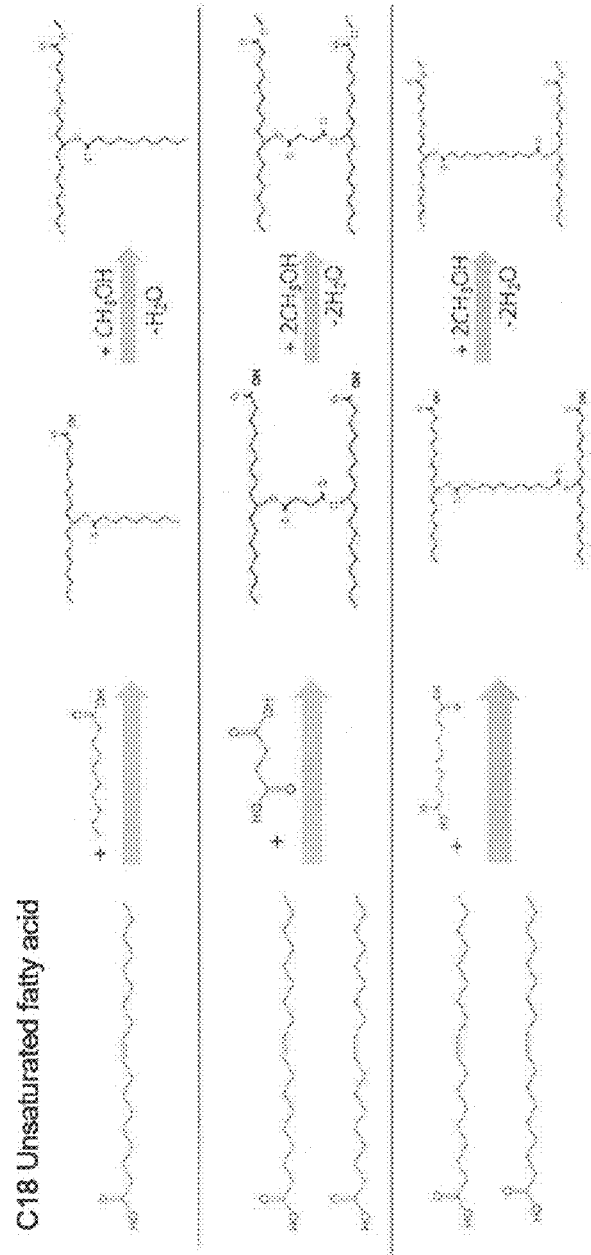
FIG. 2b illustrates the reaction mechanisms for producing estolides from C18 unsaturated fatty acid according to an aspect of the present invention.

FIG. 2 illustrates the reaction mechanisms for producing estolides according to an aspect of the present invention. As illustrated in FIG. 2, the C16 saturated fatty acid undergoes decarbonylation to give a C15 linear internal olefin, which is then subjected to an estolide reaction using, as a linking agent, 1-decanoic acid, succinic acid, or sebacic acid, thus obtaining an estolide A. Also, the C18 unsaturated fatty acid is subjected to an estolide reaction using, as a linking agent, 1-decanoic acid, succinic acid, or sebacic acid and then esterification, thus obtaining an estolide B. Also, the C18 saturated fatty acid undergoes decarbonylation to give a C17 linear internal olefin, which is then subjected to an estolide reaction using, as a linking agent, 1-decanoic acid, succinic acid, or sebacic acid, thus obtaining an estolide C.

Below is a detailed description of the present invention with reference to FIGS. 1 and 2.

Conversion of Biomass-Derived Oil into Fatty Acid

A biomass-derived oil component mainly contains triglycerides and fatty acids. Triglycerides are present in the form of three fatty acids that are ester-linked to glycerol. As such, the ratio (by weight) of triglyceride to fatty acid in the biomass-derived oil is, for example, about 100:1 to 6:1, particularly about 20:1 to 6:1, and more particularly about 10:1 to 6:1, but may vary depending on the source of biomass and is not necessarily limited to the above numerical ranges. More typically, triglycerides may constitute about 90 to 95 wt % of biomass-derived oil.

Also, the carbon chains of the triglycerides are generally composed of C4 to C24, and more typically of C16 and C18. Such triglycerides, or some mono- and di-glycerides, may be converted into mixed C16 and C18 fatty acids through de-esterification, as represented by Scheme 1 below.

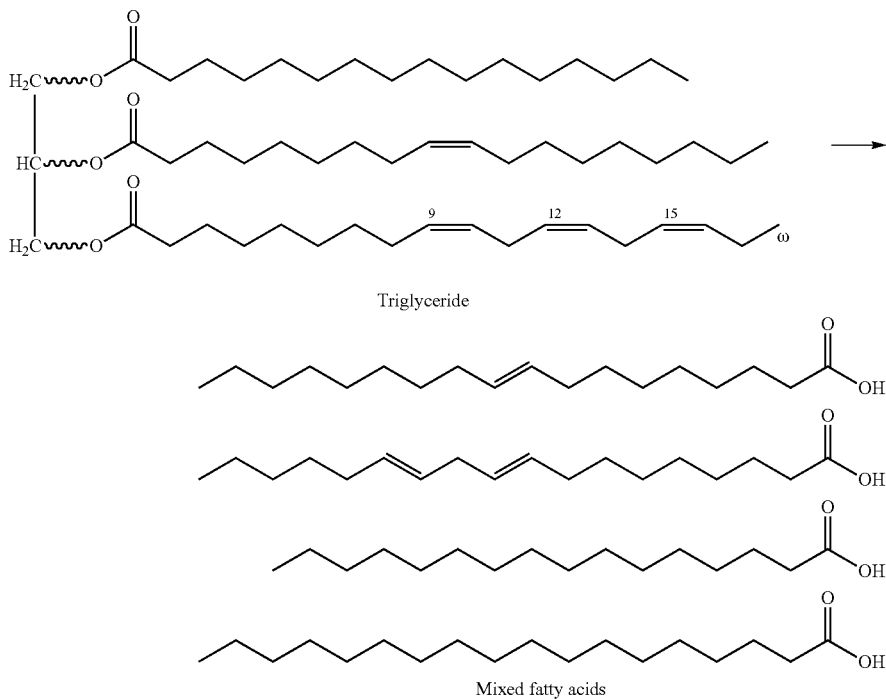

De-esterification, illustrated above, is a typical reaction for preparing fatty acid methyl ester (FAME) from biomass.

In an exemplary embodiment, de-esterification enables the conversion of triglycerides into fatty acids in the presence of a strong acid (e.g. $H_2SO_4$, $HNO_3$, HCl, HBr, HI, $HClO_4$, $HClO_3$, $HBrO_4$, $HBrO_3$, $HIO_4$, $HIO_3$, etc.) or a strong base (e.g. NaOH, KOH, $Ca(OH)_2$, an amine compound, etc.) or steam at high temperature (typically about 100 to 300° C., and more typically about 100 to 200° C.).

Also, ester bonds of triglycerides may be hydrolyzed, thus affording fatty acids. In addition, various reactions for converting triglycerides into fatty acids as known in the art may be adopted without particular limitation.

Separation of C16 Saturated Fatty Acid and C18 Unsaturated Fatty Acid

Biomass-derived oil contains various kinds of saturated fatty acids and unsaturated fatty acids. Examples of fatty acids derived from palm oil may include myristic acid, palmitic acid, oleic acid, linoleic acid, linolenic acid, monoglycerides, and diglycerides. Various kinds of fatty acids have different boiling points, whereby desired fatty acids may be selectively extracted and separated through fractional distillation.

Thus, the converted biomass-derived fatty acids may be separated and extracted into a C16 saturated fatty acid (b.p. 300 to 355° C.) and a C18 unsaturated fatty acid (b.p. 355 to 380° C.) through fractional distillation. As necessary, a C18 saturated fatty acid may be further separated. The C16 saturated fatty acid may be palmitic acid, and the C18 unsaturated fatty acids may include oleic acid, linoleic acid, and linolenic acid. The C18 saturated fatty acid is stearic acid.

Conversion of C16 Saturated Fatty Acid into Linear Internal Olefin (LIO)

As for conversion of the C16 saturated fatty acid into LIO, a biomass-derived fatty acid may be converted into LIO by inducing decarbonylation using a batch reactor in the presence of a metal chelate catalyst. In an example, the biomass-derived fatty acid is mostly composed of C16 and C18 fatty acids, and thus when decarbonylation is carried out, such fatty acids may be converted into C15 and C17 LIOs. As such, the fatty acid composition may vary depending on the source of biomass, but the present invention is not necessarily limited thereto.

The catalyst for use in decarbonylation may include a transition metal chelate catalyst, but the invention is not limited thereto. So long as an olefin, that is, a double bond, may be produced from the fatty acid, any catalyst may be used without limitation.

The transition metal may include, for example, Group 8 to 10 metals in the periodic table, and specific examples thereof may include Pd, Rh, Ir, Cu, and Fe. Also, a ligand, serving as a chelating agent, may include a phosphorus-based ligand, especially a phosphine-based ligand. Specific examples of the phosphine-based ligand may include triphenylphosphine, and diphenylphosphine-C4-7 paraffin. The amount of the ligand may be set to, for example, about 1 to 50 mol, particularly about 1 to 20 mol, and more particularly about 1 to 10 mol per mole of transition metal in the catalyst. Also, in order to increase decarbonylation activity or to control the position of the double bond in the olefin product, CO and at least one halogen element may be additionally introduced as the chelating agent into the catalyst. The halogen element may be exemplified by chlorine (Cl).

Scheme 2 below represents the reaction mechanism for decarbonylation in the presence of a transition metal chelate catalyst represented by Chemical Formula 16 below.

[Scheme 2]

[Chemical Formula 16]

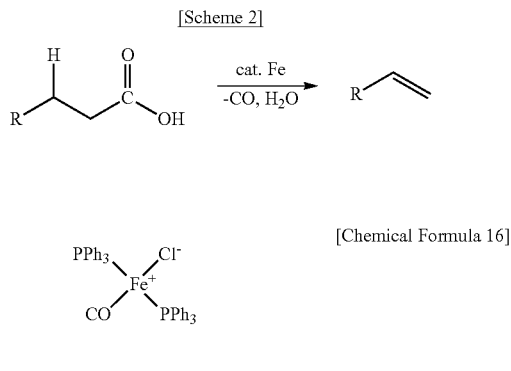

Meanwhile, an acid anhydride may be selectively added to the reaction system to remove $H_2O$ produced by decarbonylation as described above and to induce polycondensation of fatty acids so that decarbonylation can be continuously performed. Examples of the acid anhydride may include acetic anhydride and propionic anhydride, and the molar ratio of fatty acid and acid anhydride may be 1:2 to 1:50, particularly 1:2 to 1:20, and more particularly 1:2 to 1:10. The acid anhydride may be introduced into the reaction system in a CO or $N_2$ atmosphere.

Decarbonylation may be performed at a reaction temperature of about 120 to 400° C., particularly about 150 to 300° C., and more particularly about 180 to 250° C. and at a CO pressure of about 50 bar or less, particularly, about 30 bar or less, and more particularly about 1 to 20 bar.

Decarbonylation may be performed using a batch reactor or a continuous flow reactor.

Useful as a decarbonylation feed, the fatty acid mixture may contain, as a fatty acid that is derived from a triglyceride or a free fatty acid that is already present, a predetermined amount of unsaturated fatty acid having a double bond in the molecular structure thereof. Hence, this reaction may be carried out at a lower temperature than decarbonylation of only saturated fatty acids.

For decarbonylation, it is noted that the position of the double bond of the produced olefin mixture has a significant influence on the properties of the final estolide compound.

As the result of decarbonylation, a double bond is formed at the α-position of α-olefin, which is the product in the reaction mechanism. As such, the double bond may be shifted to the center of the carbon chain depending on the reaction conditions, thus obtaining an internal olefin. Furthermore, a double bond that is already present in the fatty acid before decarbonylation may be shifted.

When the temperature and time of the decarbonylation reaction are controlled, the selectivity for α-olefin or internal olefin may be controlled. For example, when the decarbonylation reaction temperature is lowered and the reaction time is shortened, the selectivity for α-olefin in the produced olefin may increase. In contrast, when the decarbonylation reaction temperature is raised and the reaction time is increased, the selectivity for internal olefin may increase.

Specifically, decarbonylation may be carried out at a temperature lower than about 250° C., and particularly lower than about 240° C. In an example, a fatty acid distillate such as PFAD may be subjected to decarbonylation in the temperature range of about 180 to 250° C. Here, the reaction time may be about 1 to 600 min, particularly about 1 to 180 min, and more particularly about 1 to 60 min. When decarbonylation is carried out at about 240° C., the double bond at the α position in the produced olefin may be shifted to thus form an internal olefin. The amount of α-olefin in the olefin mixture may be about 0 to 80 mol %, and particularly about 0 to 70 mol %, but the present invention is not necessarily limited thereto. As the reaction conditions for decarbonylation are appropriately controlled, the desired ratio of α-olefin and internal olefin may be realized.

In addition, conversion of the C16 saturated fatty acid into a linear internal olefin may be performed using partial hydrogenating and dehydration, whereby C16 and C18 fatty acids are converted into C16 and C18 linear internal olefins. Specifically, a fatty acid is converted into a fatty alcohol through partial hydrogenating, and the fatty alcohol is converted into a linear internal olefin through dehydration.

In an embodiment, the conversion of fatty acid into alcohol through partial hydrogenating may be performed using various kinds of catalysts. The catalyst may include a transition metal corresponding to Group 8 to 10 metals in the periodic table, and specific examples thereof may include Pd, Rh, Ir, Cu, and Fe.

Partial hydrogenating may be carried out at a temperature of about 120 to 500° C., particularly about 150 to 350° C., and more particularly about 200 to 300° C., and at an $H_2$ pressure of about 50 bar or less, particularly about 30 bar or less, and more particularly about 1 to 20 bar.

Partial hydrogenating may be carried out using a batch reactor or a continuous reactor. The use of a fixed-bed reactor is favorable for large-scale commercial application. This reaction may be carried out under operating conditions of a space velocity (WHSV) of about 0.05 to 10 $h^{-1}$, particularly about 0.1 to 3 $h^{-1}$, and more particularly about 0.5 to 2 $h^{-1}$ and a gas oil ratio (GOR) of about 50 to 5,000, particularly about 300 to 2,500, and more particularly about 500 to 1,500.

The conversion of fatty acid into alcohol may include converting fatty acid into ester and producing alcohol from ester through hydrogenation, especially partial hydrogenating. Although the above two steps are sequentially carried out, the reactions are very fast, and thus operating conditions for decreasing the yield of ester as an intermediate product may be determined. Hence, in the conversion of fatty acid into alcohol, an alcohol may be additionally fed to facilitate the conversion into the intermediate product, namely the ester. The fed alcohol may be inexpensive alcohol, for example, methanol.

An acid is added with an alcohol so that esterification occurs, thus producing an ester, which is then converted into an alcohol, as represented by Scheme 3 below.

[Scheme 3]

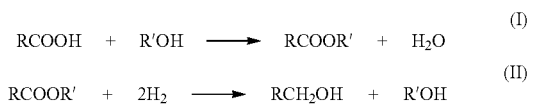

As shown in Scheme 3, the alcohol added to convert the fatty acid into the alcohol undergoes no structural changes even after the reaction, and can thus be recovered and reused.

Alternatively, the reaction may be induced using only the fatty acid, without the addition of an alcohol, as represented by Scheme 4 below.

[Scheme 4]

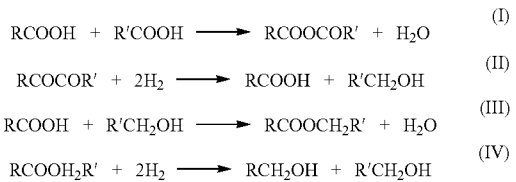

As shown in Scheme 4, even when no alcohol is additionally used, the fatty acid may be converted into a condensation polymer (an acid anhydride), which may then be converted into an ester and then an alcohol.

The converted fatty alcohol may be converted into an olefin through dehydration in the presence of a metal oxide catalyst using a fixed-bed reactor.

In an exemplary embodiment, the metal oxide catalyst for use in dehydration may be used without limitation, as long as it has a weak acid site. For example, a material having a weak acid site, such as zirmonia, may be treated under the condition that the reaction temperature is increased, whereas a material having a strong acid site, such as zeolite, may be treated under the condition that the reaction temperature is decreased, thereby enabling control of the shift in position of the double bond in the olefin. The metal oxide catalyst may be exemplified by alumina, silica-alumina, zirconia, titania, iron oxide, vanadium oxide, zeolite, and alumina-loaded mesoporous silica.

Dehydration may be carried out at 250 to 500° C., and the position of the double bond in the olefin may be shifted during the reaction depending on the extent of dehydration.

When the reaction conditions are controlled in this way, the produced olefin is not linear alpha olefin (LAO) but linear internal olefin (LIO), and the double bond position distribution in the linear internal olefin may also be controlled.

Dehydration may be carried out using a fixed-bed reactor. The inert gas injected into the fixed-bed reactor may be exemplified by nitrogen ($N_2$), argon (Ar), and helium (He), and the injected amount thereof may be 10 to 1000 sccm, and particularly 30 to 200 sccm.

The space velocity (WHSV) for the fixed-bed reactor may be 0.01 to 50 $h^{-1}$, and particularly 0.1 to 3 $h^{-1}$.

When the conditions for dehydration are appropriately controlled, a centered olefin, in which the double bond in the olefin is positioned at the center of the main chain, may be exclusively obtained. However, when a catalyst having very high or low activity is used, taking into consideration operating stability, all or some of the linear internal olefins obtained after dehydration may be recycled, thus maximizing the amount of the centered olefin in which the double bond is positioned at the center of the main chain.

Estolide Reaction Between C15 Linear Internal Olefin and Linking Agent

In an exemplary embodiment, a C15 linear internal olefin and a linking agent are subjected to an estolide reaction, thus obtaining an estolide.

The typical reaction for producing estolides is an acid-catalyzed reaction. The most useful acids are strong acids, such as $H_2SO_4$ or $HClO_4$; acids having intermediate strength such as formic acid may be used, but more severe conditions are required. The estolide reaction does not occur as rapidly as typical oligomerization and alkylation, thus causing no side reactions and taking a long period of time under the estolide reaction conditions, thereby increasing the estolide yield.

In the estolide reaction, a strong acid catalyst such as $H_2SO_4$ or $HClO_4$ may be added in an amount of about 0.5 to 10 wt % relative to the amount of feed. When a cationic catalyst such as zeolite or clay is used instead of the strong acid catalyst, it may be added in an amount of 1 to 80 wt %. When the acid catalyst is used, the reaction is carried out under the conditions of a reaction temperature of 30 to 300° C. and an $N_2$ pressure of 1 to 20 bar, and typically at 45 to 150° C. and an $N_2$ pressure of 1 bar. However, when reduced pressure is applied to suppress side reactions, the reaction may be carried out at a lower temperature. When zeolite or clay is used, the reaction is carried out under the conditions of a reaction temperature of 150 to 380° C. and an $N_2$ pressure of 1 to 10 bar. The estolide is produced using a batch reactor, and the estolide reaction does not occur as rapidly as typical polymerization, and thus the stirring rate is regarded as important. This reaction is implemented at a stirring rate of 200 to 7000 rpm. Although the reaction may become more efficient with an increase in the stirring rate, it is typically carried out at 500 to 1000 rpm taking into consideration the device stability. When the cationic catalyst such as zeolite or clay is used, the use of a batch reactor is typical, but a fixed-bed reactor may be applied. However, when a fixed-bed reactor is used, the catalyst may become inactivated due to coking, and the reaction activity may decrease. Hence, the use of such a fixed-bed reactor is considered to be unfavorable.

The method of producing estolides according to the present invention is quite different from conventional estolide production methods in that it uses a linking agent in dicarboxylic acid form. Although a linking agent is used, the same estolide reaction conditions and processing are applied. The linking agent may include any dicarboxylic acid, tricarboxylic acid, or polycarboxylic acid, as known in the art. The linking agent may function to improve the properties of the lubricating oil, such as the viscosity, viscosity index, pour point, cloud point, etc. Examples of dicarboxylic acid may include linear dicarboxylic acid, such as oxalic acid, succinic acid, and sebacic acid, and branched dicarboxylic acid. Tricarboxylic acid such as citric acid or iso-citric acid may also be used. More particularly, the linking agent may be provided in the form of dicarboxylic acid, and may include, for example, oxalic acid, malonic acid, succinic acid, glutaric acid, adipic acid, pimelic acid, suberic acid, azelaic acid, sebacic acid, or 1-decanoic acid.

Partial Hydrogenation of C18 Unsaturated Fatty Acid

A C18 unsaturated fatty acid is subjected to partial hydrogenating, so that in the biomass-derived oil, linoleic acid (C18:2) or linolenic acid (C18:3) may be converted into oleic acid (C18:1), thereby increasing the amount of oleic acid.

The catalyst for use in partial hydrogenating is configured such that NiMo, CoMo, or Mo metal is loaded on a water-resistant carrier. Also, the hydrogenating process according to the present invention is different from a conventional hydrogenating process in terms of the peculiarities of biomass itself. Biomass has very high oxygen content compared to crude oil. When oxygen is removed through the hydrogenating reaction, this oxygen may be removed in the form of $H_2O$ through the reaction with hydrogen, thus melting the active metal and the carrier of the catalyst, undesirably and seriously causing the inactivation of the catalyst. Hence, hydrogenating of biomass may be seriously problematic because the catalyst may be inactivated due to the water byproduct. In the present invention, a water-resistant carrier such as $ZrO_2$, $TiO_2$, etc. is used, thereby overcoming the problem of inactivation of the catalyst owing to catalyst leaching.

Partial hydrogenating may be carried out under operating conditions of a temperature of 160 to 180° C. and a pressure of 20 to 40 bar, rather than typical hydrogenating conditions of a high temperature of 200° C. or more and a high pressure of 40 bar or more. In the case where the reaction is implemented under conditions of a high temperature of 180° C. or more and a high pressure of 40 bar or more, unsaturated double bonds may completely disappear unlike the original intension, and thus stearic acid (C18:0) may be produced, and in more severe cases, decarboxylation may occur, thus causing side reactions in which C15 and C17 linear paraffins may be produced.

For this reason, the reaction, which enables an olefin having two or more unsaturated double bonds in the biomass-derived oil to be partially saturated so that only one unsaturated double bond is present, has to be carried out under the limited reaction conditions described above. Even if some of the olefins having two or more unsaturated double bonds may be converted into olefins having a single unsaturated double bond under the above limited reaction conditions, when recycling is performed, all of the olefins having two or more unsaturated double bonds may be consequently processed, and thus the suppression of side reactions is regarded as more important than the reaction yield.

Estolide Reaction Between Oleic Acid and Linking Agent

The estolide reaction between oleic acid and a linking agent is the same as the estolide reaction between the C15 linear internal olefin and the linking agent as described above, with the exception that oleic acid is used, instead of the C15 linear internal olefin.

Esterification

In order to stabilize the produced estolide into an ester, an alcohol such as methanol is added, or esterification may be induced using a branched alcohol to increase steric hindrance. The alcohol is added in excess, and is specifically added in an amount 1 to 100 times as large as the amount of acid (in mol %). Esterification is typically carried out at 100° C. or less using a strong acid catalyst such as $H_2SO_4$, as in the estolide reaction. Acid-catalyzed esterification may rapidly occur within 6 hr. The stirring rate therefor may be set to 200 rpm or more, which is merely equal to or higher than a predetermined level. In order to increase structural stability, a branched alcohol may be employed.

In an exemplary embodiment, the estolides produced according to an embodiment of the present invention may be represented by Chemical Formulas 1 to 15 below.

[Chemical Formula 1]

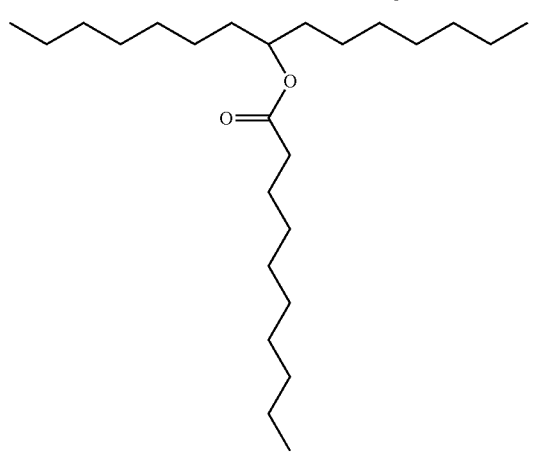

[Chemical Formula 2]

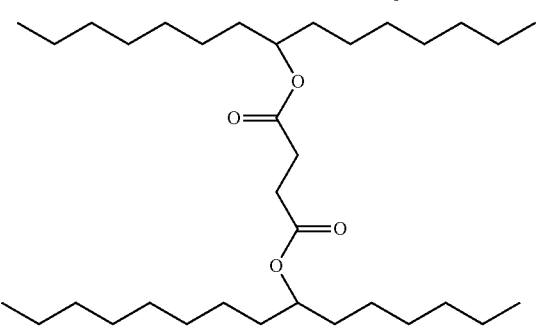

[Chemical Formula 3]
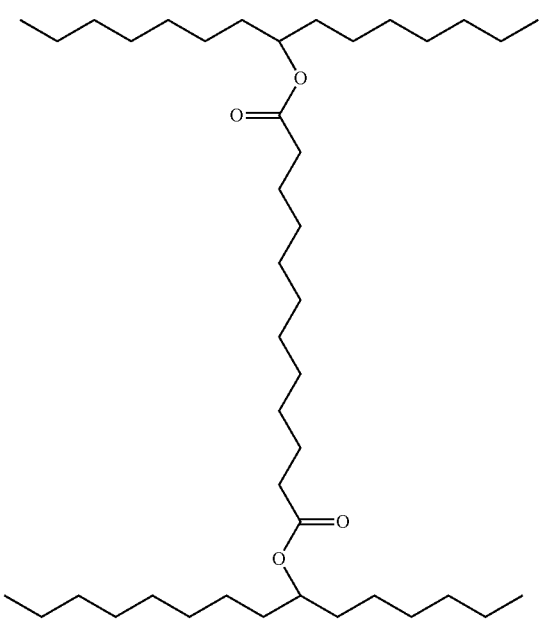
[Chemical Formula 4]
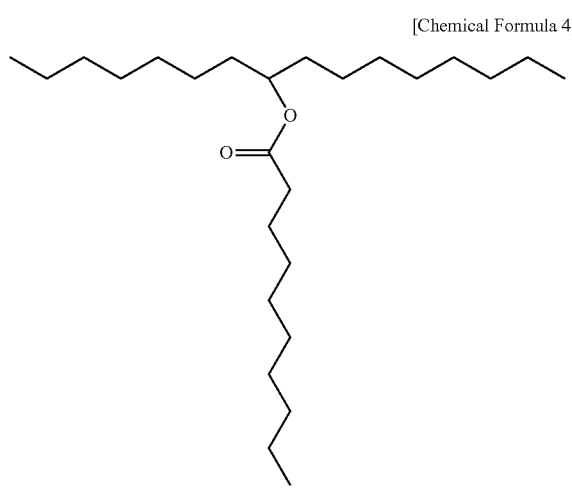
[Chemical Formula 5]
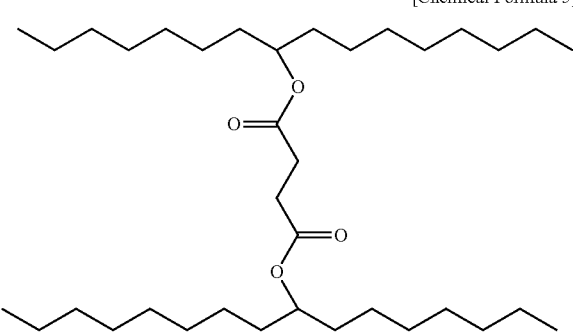
[Chemical Formula 6]
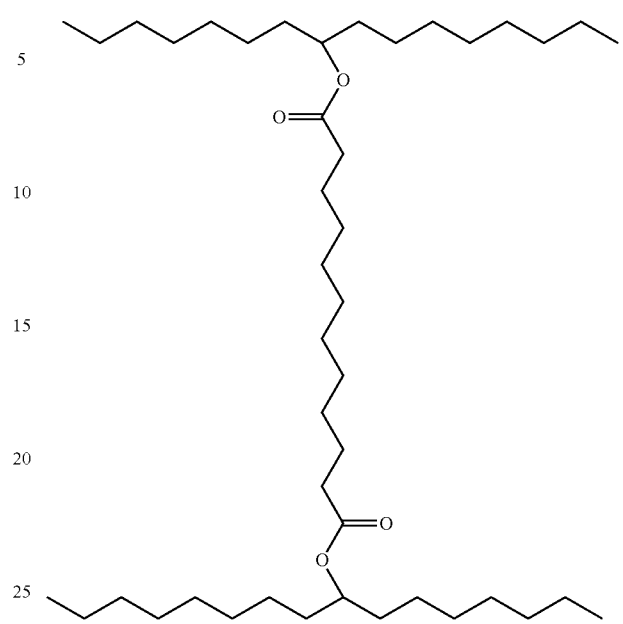
[Chemical Formula 7]
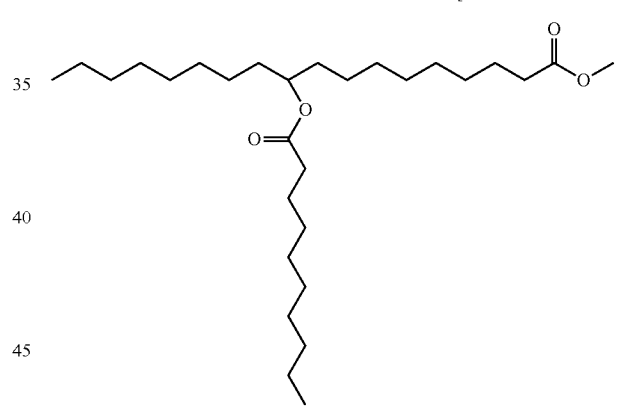
[Chemical Formula 8]
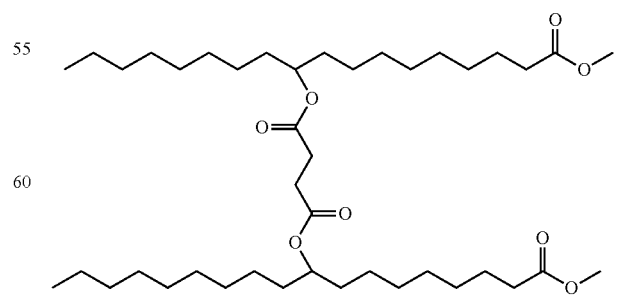

[Chemical Formula 9]
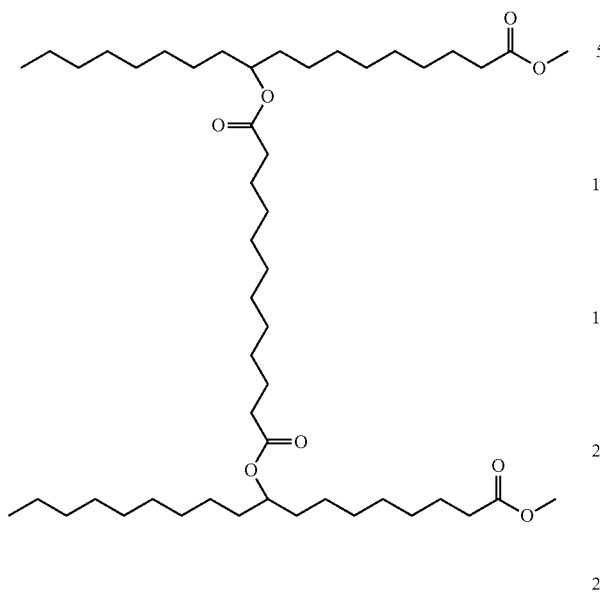
[Chemical Formula 10]
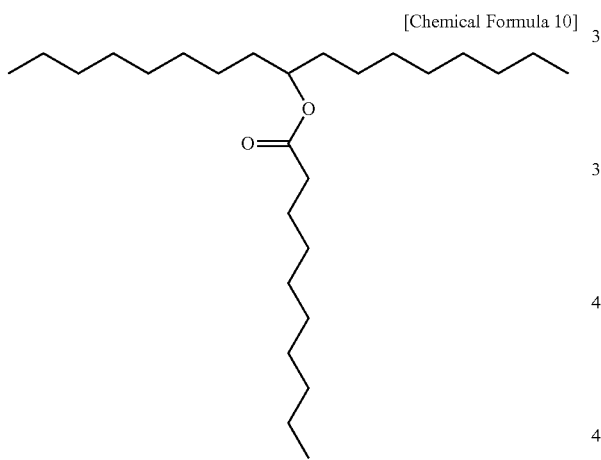
[Chemical Formula 11]
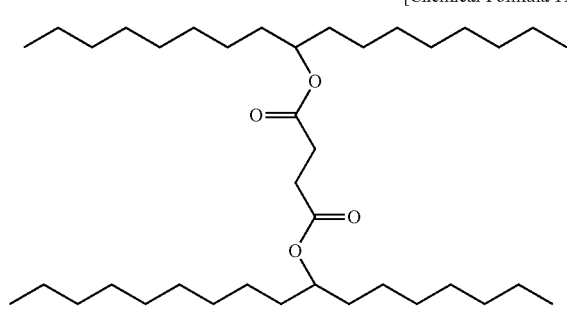
[Chemical Formula 12]
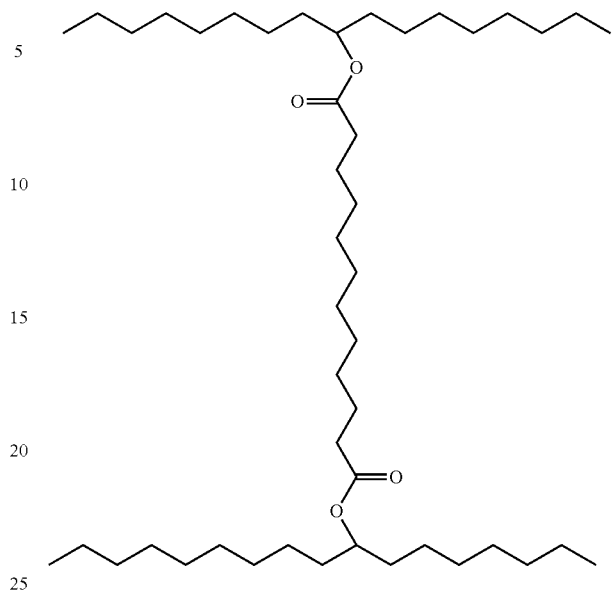
[Chemical Formula 13]
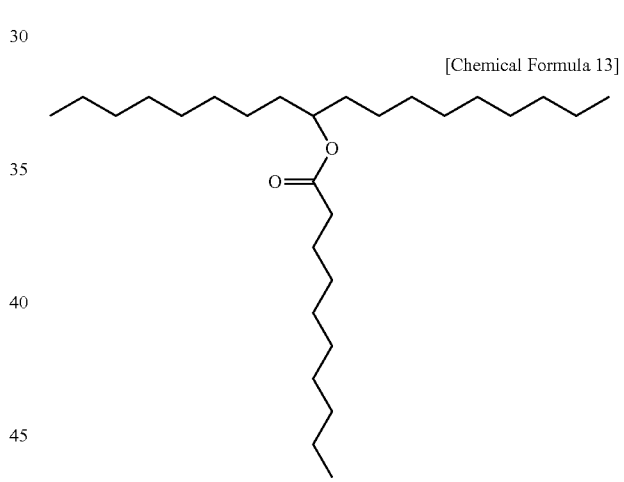
[Chemical Formula 14]
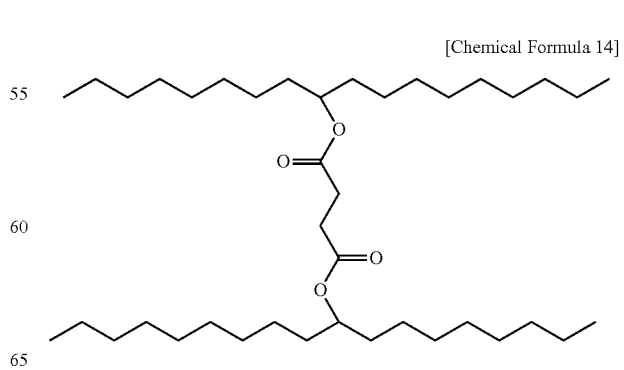

[Chemical Formula 15]

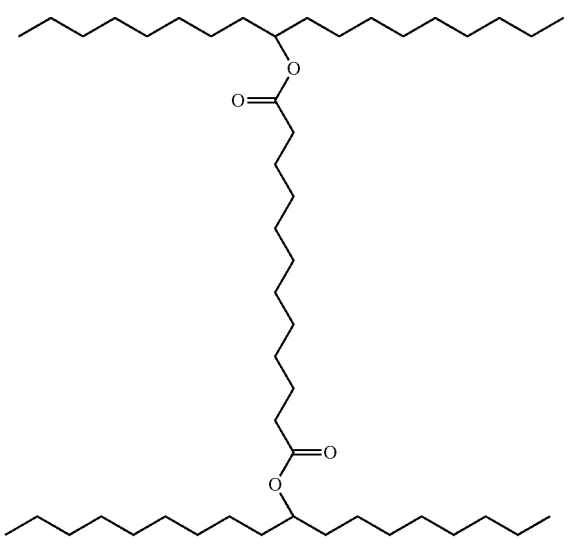

These estolides have no residual unsaturated double bonds, unlike existing estolide products, and also contain an ester functional group having high steric hindrance in the molecules thereof, advantageously making it difficult to convert the ester into an acid. Furthermore, the produced materials may be mixed, thereby manufacturing environmentally friendly lubricating base oil products that exhibit properties similar to those of conventional PAO lubricating oil.

Also, the estolides can realize the advantages of environmentally friendly lubricating oil. Examples of the advantages of lubricating oil that estolides can retain include high biodegradability, a high viscosity index, good low-temperature stability, etc.

A better understanding of the present invention may be obtained via the following examples which are set forth to illustrate, but are not to be construed as limiting the present invention.

Example 1

A. Separation of Fatty Acid

Figure 3:
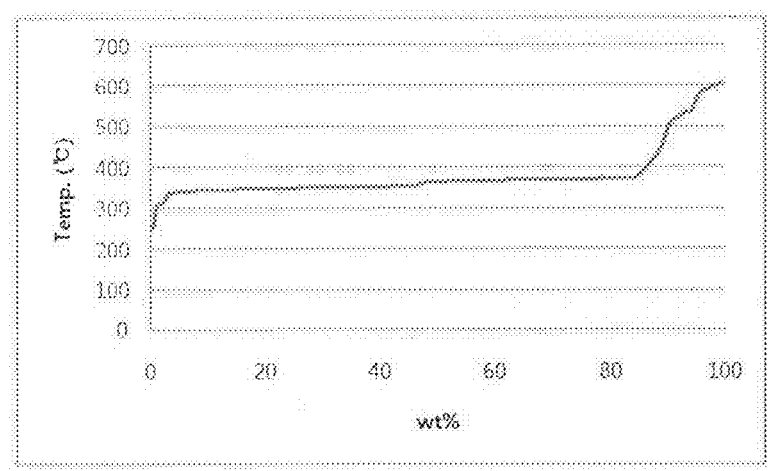
FIG. 3 is a graph illustrating the results of SimDist analysis of palm fatty acid distillate (PFAD) of Example 1.

The composition of PFAD (palm fatty acid distillate) was analyzed through SimDist, and 2.2 kg of PFAD was placed in a TBP cutting device, and fatty acids were thereby separated depending on the reaction temperature. Based on the results of SimDist analysis of PFAD, the pattern of FIG. 3 appeared.

PFAD was cut at 300° C., 355° C., and 380° C., thus obtaining individual fatty acids in the amounts shown in Table 2 below.

TABLE 2

| Fatty acid | PFAD composition (wt %) |
| --- | --- |
| 14:0 Myristic acid | 3 |
| 16:0 Palmitic acid | 43 |
| 18:1, 18:2, 18:3 Oleic acid, Linoleic acid, Linolenic acid | 38 |
| Mono-glyceride, Di-glyceride | 16 |
| Total | 100 |

The PFAD sample was separated into myristic acid (b.p. <300° C.), palmitic acid (b.p. 300 to 355° C.), C18 fatty acid (b.p. 355 to 380° C.), and mono- and di-glycerides (b.p. >380° C.) through cutting at 300° C., 355° C., and 380° C. The amounts of the fatty acids thus separated are shown in Table 3 below.

TABLE 3

| Fatty acid | Separated sample amount (g) |
| --- | --- |
| 14:0 Myristic acid | 59 |
| 16:0 Palmitic acid | 957 |
| 18:1, 18:2, 18:3 Oleic acid, Linoleic acid, Linolenic acid | 807 |
| Mono-glyceride, Di-glyceride | 313 |
| Total | 2136 |

B. Maximization of Oleic Acid Yield Through Partial Hydrogenating Using Catalyst 807 g of the C18 linear olefinic fatty acid obtained as above was subjected to partial hydrogenating using a NiMo/$ZrO_2$ catalyst, and was thereby completely converted into oleic acid. The NiMo/$ZrO_2$ catalyst used was prepared as follows.

Specifically, the catalyst was prepared by loading about 10 wt % of Mo and about 3 wt % of Ni on a $ZrO_2$ carrier having a diameter of 1 mm. The Mo precursor was ammonium heptamolybdate tetrahydrate (AHM), and the Ni precursor was nickel nitrate hexahydrate (NNH) (Mo and Ni were fed using various precursors, but the invention is not limited thereto).

More specifically, an aqueous solution of AHM dissolved in deionized (DI) water was incorporated in a $ZrO_2$ carrier, dried at about 150° C. for about 2 hr, and continuously burned at about 500° C. for about 2 hr, thus preparing Mo/$ZrO_2$.

Then, NNH was dissolved in DI water, impregnated with the Mo/$ZrO_2$ catalyst, dried at about 150° C. for about 2 hr, and continuously burned at about 500° C. for about 2 hr, yielding the NiMo/$ZrO_2$ catalyst.

6 cc of the catalyst thus prepared was placed in a cylindrical reactor, loaded with an R-LGO feed at a rate of 0.08 cc/min at room temperature, heated to 320° C. under conditions of a reaction pressure of 45 bar and an $H_2$ flow rate of 16 cc/min, and pretreated for 3 hr at 320° C.

6 g of the NiMo/ZrO catalyst thus pretreated was placed in a fixed-bed reactor, after which 807 g of the C18 linear olefinic fatty acid mixture obtained in "A" above and 8.1 g of dimethyl disulfide (DMDS) were reacted at a rate of 0.1 cc/min (LHSV=1) under conditions of a reaction temperature of 180° C., a reaction pressure of 20 bar, and an $H_2$ flow rate of 100 cc/min. Sampling was conducted at 8-hr intervals, the properties of the obtained products were measured through GC-MS, and the leaching of the catalyst was checked using ICP.

Based on the results of analysis of GC-MS, as shown in Table 4 below, C18:2 and C18:3 were selectively converted into C18:1.

Although linoleic acid was not completely converted into oleic acid, conversion thereof into oleic acid was possible through recirculation treatment. The reason why linolenic acid was found to remain in a small amount is considered to be because unreacted feed, produced during the initial reaction, is mixed in a small amount.

TABLE 4

| A series | A, Feed A | A, 180-20 |
| --- | --- | --- |
| Myristic acid (14:0) | 0.0 | 0.0 |
| Palmitic acid (16:0) | 0.0 | 0.0 |

TABLE 4-continued

| A series | A, Feed A | A, 180-20 |
|---|---|---|
| Stearic acid (18:0) | 0.0 | 0.0 |
| Oleic acid (18:1) | 80.3 | 93.9 |
| Linoleic acid (18:2) | 17.9 | 5.9 |
| Linolenic acid (18:3) | 1.8 | 0.2 |

The above product was placed in a 500 cc flask to undergo fractional distillation using a Spaltrohr HMS 300 C made by Fischer technology, ultimately obtaining 703 g of oleic acid.

C. Production of Oleic Acid-Derived Estolide B 203.1 g of the oleic acid thus obtained was placed in a 500 cc flask, and 80.1 g of succinic acid was then added. For this, extra pure grade oleic acid, made by SamChun Chemical, and succinic acid having a purity of 99% or more, made by Sigma-Aldrich, were used. The 500 cc flask was connected with a stirring rod, a thermometer, and a cooling trap, and was stirred at 800 rpm and then heated to 210° C. When the reaction temperature reached 210° C., 7.1 g of sulfuric acid was added dropwise to the reaction system of the reactor. The sulfuric acid used was purchased from Across, and had a purity of 96% (in water). 3 hr after the addition of $H_2SO_4$, the operation was terminated and the reaction product was allowed to stand until it reached room temperature.

After termination of the reaction, the product was filtered, and unreacted succinic acid was separated. The amount of the separated succinic acid was 56.3 g. 214.0 g of the remaining solution was placed in a 4 L reactor, and a mixture comprising 1020 g of methanol and 31.3 g of sulfuric acid was added. The same sulfuric acid product as above, made by Across, was used, and methanol made by SamChun Chemical, having a purity of 99.8%, was used. Thereafter, the temperature of the reactor was raised to 75° C. and maintained for 3 hr. Thereafter, the reaction was terminated, and the reaction product was allowed to stand until it reached room temperature.

In order to obtain the final product, the product was recovered, and the acidity thereof was checked using a mixed aqueous solution of KOH/ethanol (KOH/EtOH/DI water=0.1 g/30 g/1975 g). The mixed solution having no remaining acid was placed in a separatory funnel and allowed to stand. When the organic layer and the water layer containing salt and alcohol were separated in the separatory funnel, the water layer was removed, and the organic layer was isolated, from which the remaining salt and acid were then removed using 2 L of DI water. The amount of the organic layer was 222.8 g.

The yield of the product was measured through SimDist analysis of the organic layer. The results are shown in Table 5 below.

TABLE 5

| Product | Wt % |
|---|---|
| Succinic acid | 1 |
| Methyl oleate | 3 |
| Mono-substituted estolide | 26 |
| Oleic acid estolide (dimer) | 28 |
| Di-substituted estolide (desired product) | 39 |
| Oleic acid estolide (trimer) | 3 |

The obtained organic layer was further subjected to fractional distillation (Spaltrohr HMS 300 C; Fischer technology), and was cut at 480° C., thereby removing unreacted feed-derived ester, mono-substituted estolide and oleic acid estolide. Ultimately, the amount of the separated material obtained through cutting at 480° C. was 128.1 g and the amount of the product at 480° C. or more was 90.5 g.

D. Analysis of Properties of Estolide B

The properties of the estolide B produced in Example 1 as a lubricating oil were analyzed for pour point (PP), viscosity (40° C., 100° C.), and iodine value, from which the viscosity index (VI) was then calculated. The analyzed and calculated properties of estolide as lubricating oil are shown in Table 6 below.

TABLE 6

| Estolide | Viscosity at 40° C. (Cst) | Viscosity at 100° C. (Cst) | VI | PP (° C.) | Iodine value (cg/g) |
|---|---|---|---|---|---|
| Example 1 | 29.81 | 5.71 | 136 | −37 | 0.01 |

The estolide produced in Example 1 exhibited superior lubricating oil properties in terms of VI and PP, and had almost no remaining unsaturated double bonds. This material contains about 7% oleic acid estolide (trimers), but is considered to be an estolide obtained using succinic acid, and is also regarded as a good lubricating base oil because the pour point and VI thereof are high.

Example 2

440.0 g of the C16:0 fatty acid obtained through fatty acid separation in Example 1 was placed in a 4 L autoclave reactor, after which 20.4 g of $FeCl_2$ anhydride, 168 g of triphenylphosphine, and 163.2 g of acetic anhydride were sequentially added and physically mixed together. The mixture was purged two times with $N_2$, and $N_2$ was charged at a pressure of 20 bar, whereby the total reaction pressure was set to 20 bar. Subsequently, the temperature was raised to 240° C. and maintained for 10 min, and then the reaction was shut down.

The recovered catalyst and the reaction product were filtered, thus separating the catalyst lump from the reaction product. Thereafter, the catalyst was separately stored so as to be reused, and the filtered reaction product was mixed with 2 L of DI water and stirred overnight. Thereafter, the reaction product was separated from DI water using a separatory funnel, and the separated reaction product was further filtered using Celite powder. The reaction product thus obtained was subjected to vacuum distillation (Spaltrohr HMS 300 C; Fischer technology), so that n-heptane was selectively separated from the reaction product, thereby recovering the final reaction product. The conversion efficiency for the recovered reaction product was measured through SimDist analysis, and selectivity for α-olefin in the olefin product and the occurrence of the other side reactions were evaluated through GC-MS analysis.

The reaction product was post-treated and analyzed in the same manner as in Example 1. The results are given in Table 7 below.

TABLE 7

| Run No. | Reaction Temp. (° C.) | Total yield (%) | Total product amount (g) | C15 olefin amount (g) |
|---|---|---|---|---|
| 1 | 240 | 80.3 | 355.9 | 351.0 |

Based on the results of GC-MS analysis, the C15 olefin was selectively produced, and only a small amount of trace components were present, but almost no side reactions occurred. The olefin was composed mainly of linear internal olefin, while there was almost no α-olefin. The boiling point of the produced C15 olefin was measured to be about 270° C., and the obtained liquid product was subjected to fractional distillation (Spaltrohr HMS 300 C; Fischer technology) to thereby selectively separate an oil fraction having a boiling point of about 260 to 275° C., yielding a C15 linear internal olefin.

E. Production of Estolide A 200.4 g of the linear internal olefin obtained as above was placed in a 500 cc flask, and 80.1 g of succinic acid was then added. The 500 cc flask was connected with a stirring rod, a thermometer, and a cooling trap, and was stirred at 800 rpm and then heated to 210° C. When the reaction temperature reached 210° C., 22.5 g of sulfuric acid was added dropwise to the reaction system of the reactor. The reactor was maintained for 12 hr, after which the operation was terminated and the reaction product was allowed to stand until it reached room temperature.

After termination of the reaction, the product was filtered, and unreacted succinic acid was separated. The amount of the separated succinic acid was 71.7 g. The acidity of the remaining solution, which amounted to 202.5 g, was checked using a mixed aqueous solution of KOH/ethanol (KOH/EtOH/DI water=0.1 g/30 g/1975 g). The mixed solution having no remaining acid was placed in a separatory funnel and allowed to stand. When the organic layer and the water layer containing salt and alcohol were separated in the separatory funnel, the water layer was removed, and the organic layer was isolated, from which the remaining salt and acid were then removed using 2 L of DI water. The amount of the final organic layer was 203.5 g.

The yield of the product was measured through SimDist analysis of the organic layer. The results are shown in Table 8 below.

TABLE 8

| Product | Wt % |
|---|---|
| Succinic acid | 1 |
| C15 linear internal olefin | 76 |
| Mono-substituted estolide | 10 |
| Di-substituted estolide (desired product) | 13 |

The obtained organic layer was further subjected to fractional distillation (Spaltrohr HMS 300 C; Fischer technology), and was cut at 480° C., thereby removing unreacted linear internal olefin and mono-substituted estolide. Thereby, the amount of di-substituted estolide ultimately obtained through cutting at 480° C. was 25.1 g.

The estolide yield resulting from the reaction using the linear internal olefin exhibited remarkably low reaction activity compared to when using unsaturated fatty acid.

F. Analysis of Properties of Estolide A

The properties of the estolide A thus produced as a lubricating oil were analyzed for PP, viscosity (40° C., 100° C.), and iodine value, from which the viscosity index (VI) was then calculated. The analyzed and calculated properties of estolide as lubricating oil are shown in Table 9 below.

TABLE 9

| Estolide | Viscosity at 40° C. (Cst) | Viscosity at 100° C. (Cst) | VI | PP (° C.) | Iodine value (cg/g) |
|---|---|---|---|---|---|
| Example 2 | 26.17 | 5.29 | 139 | −45 | 0.01 |

The use of the linear internal olefin resulted in low yield but superior lubricating oil properties.

Although the embodiments of the present invention have been disclosed for illustrative purposes, those skilled in the art will appreciate that the present invention may be embodied in to other specific ways without changing the technical spirit or essential features thereof. Therefore, the embodiments disclosed in the present invention are not restrictive but are illustrative.

What is claimed is:

1. A method of producing an estolide, comprising:
    a) converting biomass-derived oil into a fatty acid mixture;
    b) separating the fatty acid mixture into a C16 saturated fatty acid and a C18 unsaturated fatty acid;
    c) converting the C16 saturated fatty acid into a C15 or C16 linear internal olefin;
    d) subjecting the C15 or C16 linear internal olefin to an estolide reaction using a linking agent, thus obtaining an estolide A;
    e) subjecting the C18 unsaturated fatty acid to partial hydrogenating to increase an amount of oleic acid; and
    f) subjecting the oleic acid to an estolide reaction using a linking agent and then esterification, thus obtaining an estolide B.

2. The method of claim 1, wherein the linking agent is dicarboxylic acid, tricarboxylic acid, or polycarboxylic acid.

3. The method of claim 1, wherein the linking agent is linear dicarboxylic acid or branched dicarboxylic acid.

4. The method of claim 1, wherein the linking agent is oxalic acid, malonic acid, succinic acid, glutaric acid, adipic acid, pimelic acid, suberic acid, azelaic acid, sebacic acid, or 1-decanoic acid.

5. The method of claim 1, wherein the subjecting the C18 unsaturated fatty acid to partial hydrogenating comprises converting linoleic acid or linolenic acid into oleic acid.

6. The method of claim 1, wherein the converting the C16 saturated fatty acid into the C15 linear internal olefin is performed using decarbonylation.

7. The method of claim 1, wherein the converting the C16 saturated fatty acid into the C16 linear internal olefin is performed using partial hydrogenating for converting the C16 saturated fatty acid into a fatty alcohol and dehydrating.

8. The method of claim 1, wherein the step b) further comprises g) separating a C18 saturated fatty acid.

9. The method of claim 8, further comprising:
    h) converting the C18 saturated fatty acid into a C17 or C18 linear internal olefin; and
    i) subjecting the C17 or C18 linear internal olefin to an estolide reaction using a linking agent, thus obtaining an estolide C.

10. The method of claim 1, wherein a) is performed by subjecting triglyceride in the biomass-derived oil to de-esterification or hydrolysis.

11. The method of claim 1, further comprising j) separating or purifying the estolide A.

12. The method of claim 11, further comprising k) recirculating a linear internal olefin or mono-substituted estolide separated or purified in j) back to d).

13. The method of claim 1, further comprising l) separating or purifying the estolide B after f), or separating or purifying the estolide produced after the estolide reaction in f).

14. The method of claim 13, further comprising m) recirculating a C18 fatty acid or mono-substituted estolide separated or purified in l) back to f).

15. An estolide, comprising at least one selected from the group consisting of:
    an estolide A, configured such that a carboxylic acid functional group of a linking agent is linked to a position of a double bond in a C15 or C16 linear internal olefin;
    an estolide B in ester form, configured such that a carboxylic acid functional group of a linking agent is linked to a position of a double bond in oleic acid; and
    an estolide C, configured such that a carboxylic acid functional group of a linking agent is linked to a position of a double bond in a C17 or C18 linear internal olefin, wherein the linking agent is oxalic acid, malonic acid, succinic acid, glutaric acid, adipic acid, pimelic acid, suberic acid, azelaic acid, sebacic acid, or 1-decanoic acid.

16. The estolide of claim 15, wherein the estolide is represented by Chemical Formulas 1 to 15 below:

[Chemical Formula 1]
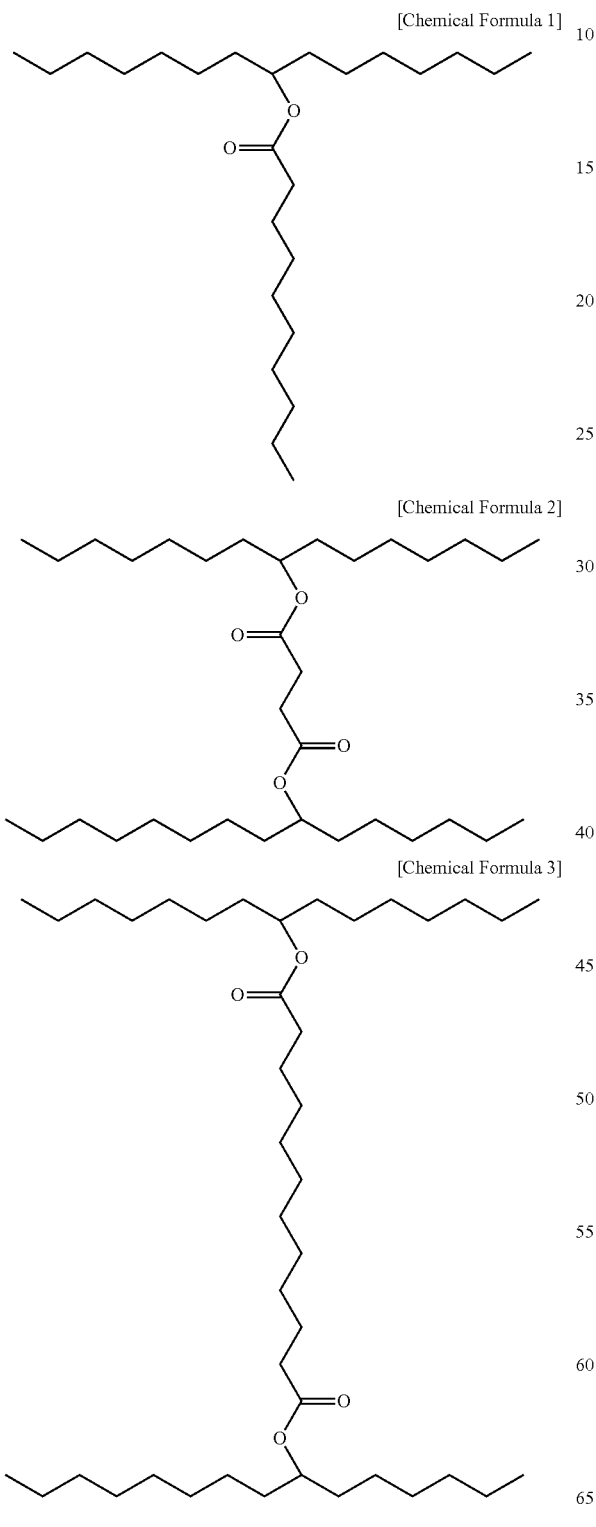

[Chemical Formula 2]

[Chemical Formula 3]

[Chemical Formula 4]
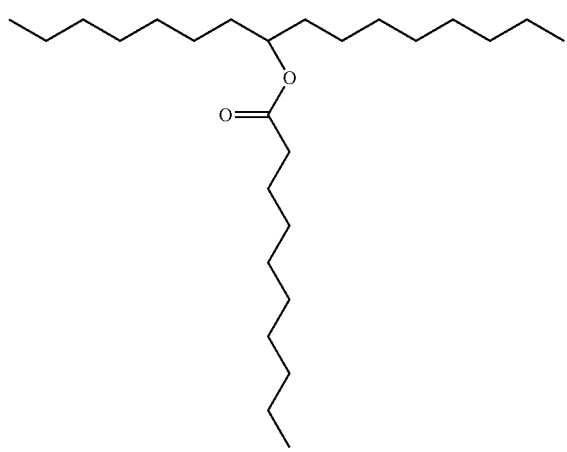

[Chemical Formula 5]
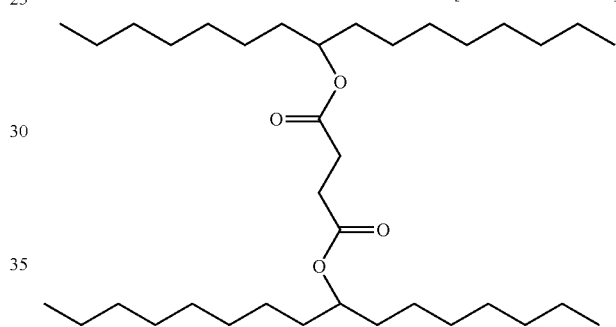

[Chemical Formula 6]
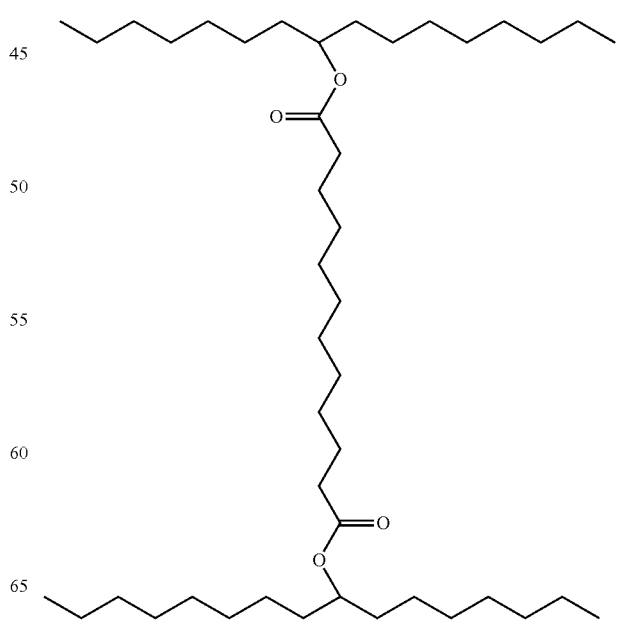

[Chemical Formula 7]
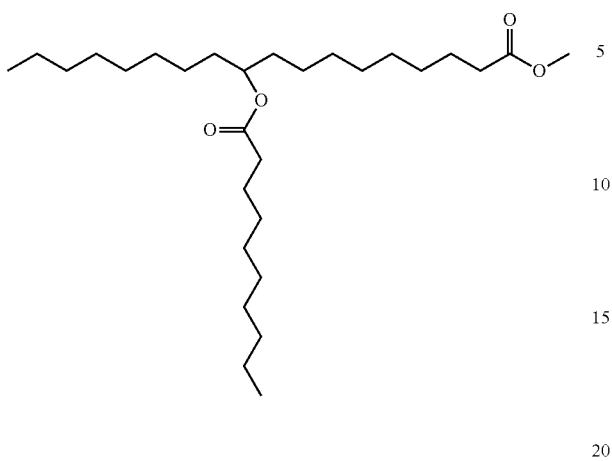
[Chemical Formula 10]
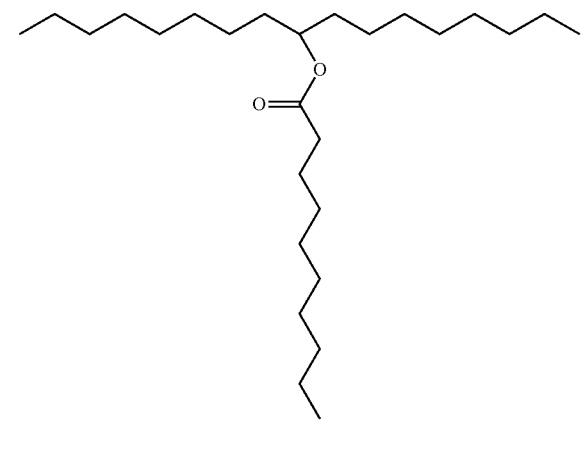
[Chemical Formula 8]
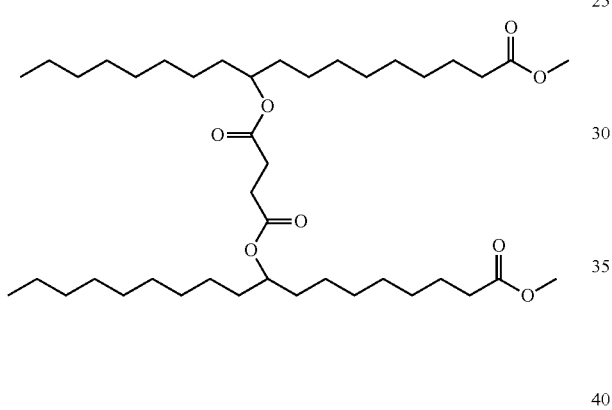
[Chemical Formula 11]
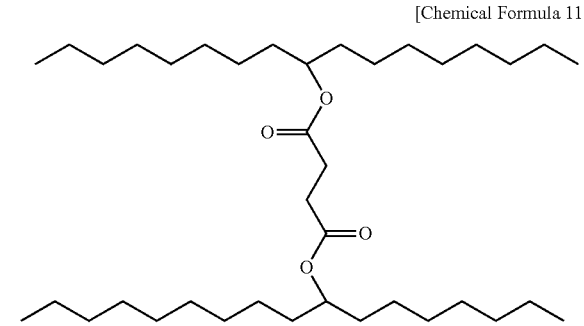
[Chemical Formula 9]
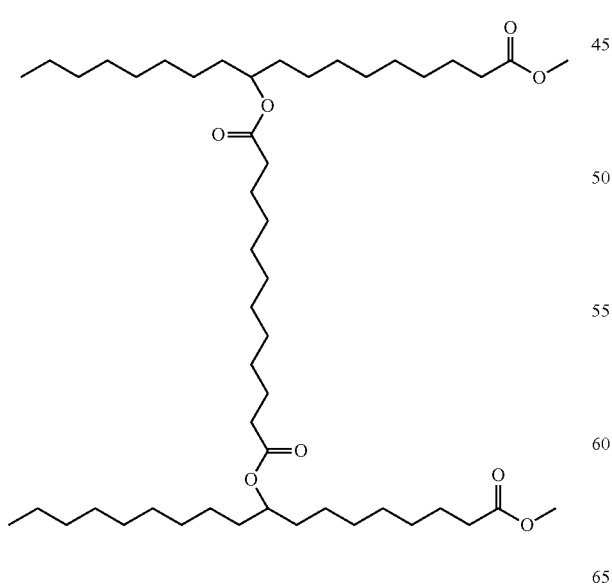
[Chemical Formula 12]
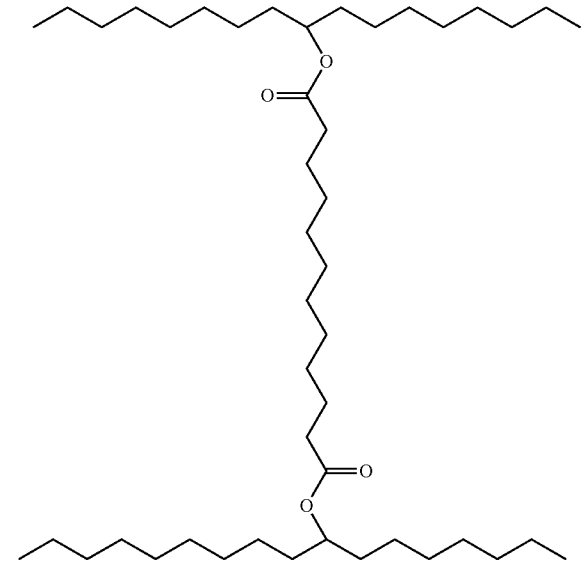

-continued

[Chemical Formula 13]

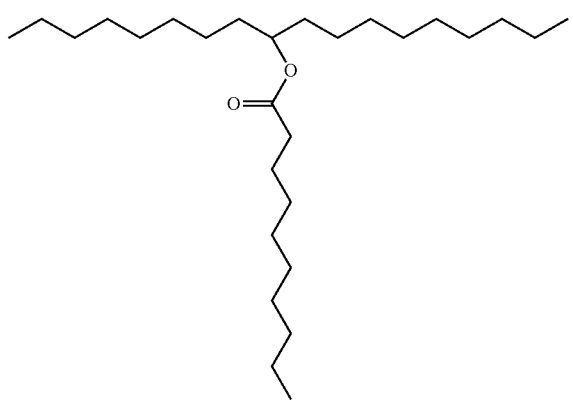

[Chemical Formula 14]

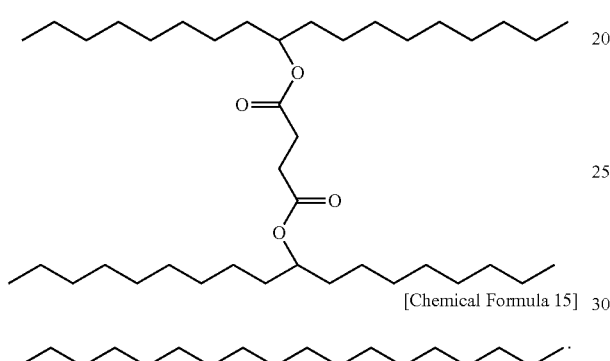

[Chemical Formula 15]

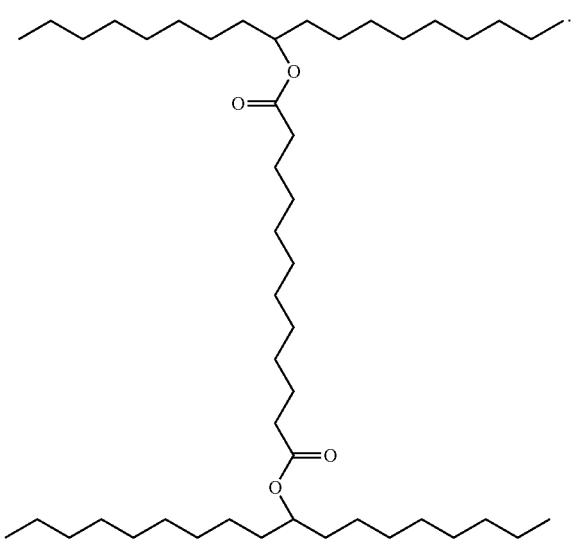

17. A lubricating oil, comprising the estolide of claim 15.
18. An estolide, comprising at least one selected from the group consisting of:
   an estolide A, configured such that a carboxylic acid functional group of a linking agent is linked to a position of a double bond in a C15 or C16 linear internal olefin;
   an estolide B in ester form, configured such that a carboxylic acid functional group of a linking agent is linked to a position of a double bond in oleic acid; and
   an estolide C, configured such that a carboxylic acid functional group of a linking agent is linked to a position of a double bond in a C17 or C18 linear internal olefin
   wherein the linking agent is dicarboxylic acid, tricarboxylic acid, or polycarboxylic acid.

19. The estolide of claim 18, wherein the dicarboxylic acid is linear dicarboxylic acid or branched dicarboxylic acid.
20. The estolide of claim 15, wherein the estolide is represented by Chemical Formulas below:

[Chemical Formula 2]

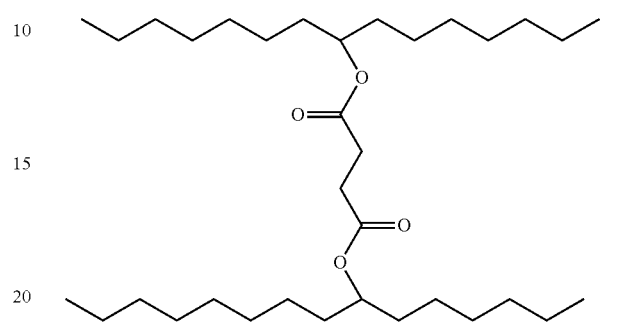

[Chemical Formula 3]

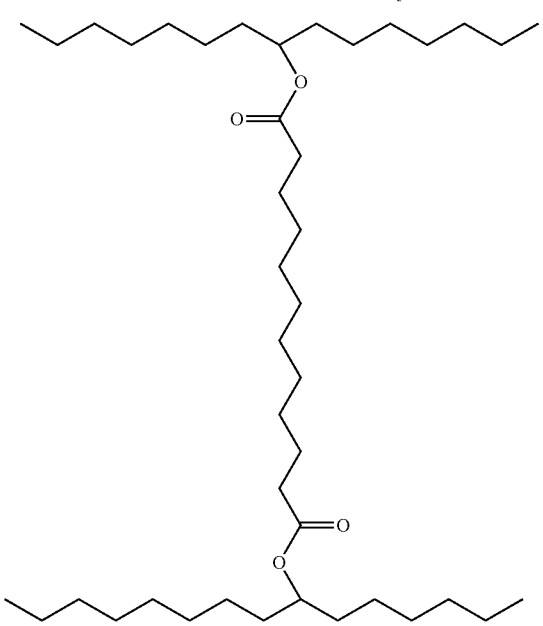

[Chemical Formula 5]

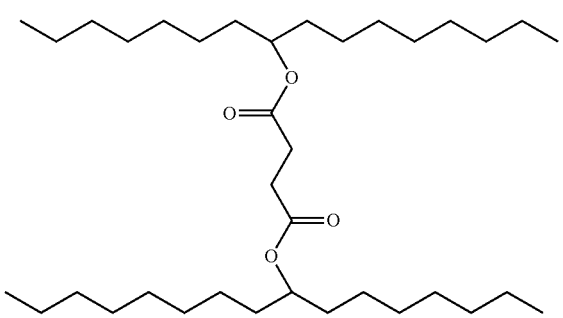

[Chemical Formula 6]
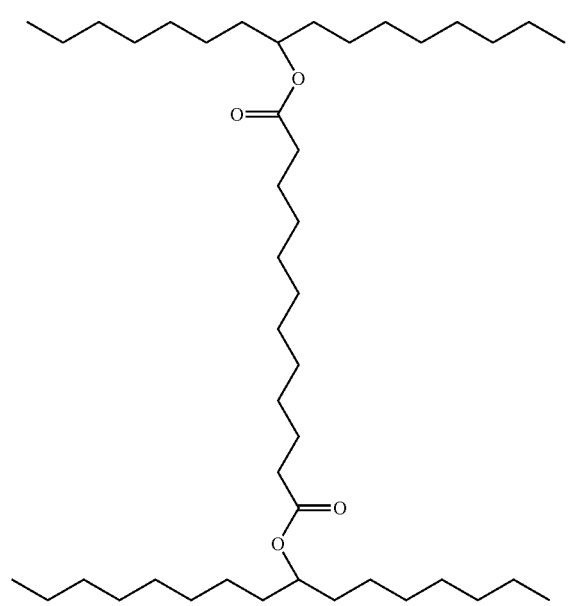
[Chemical Formula 8]
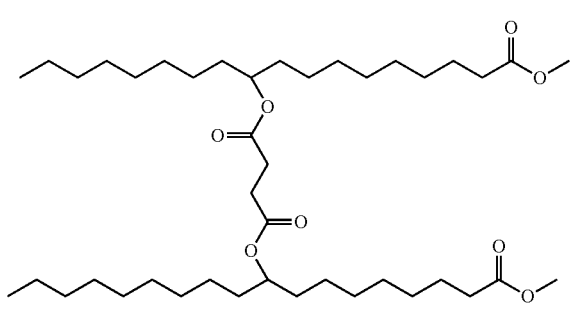
[Chemical Formula 9]
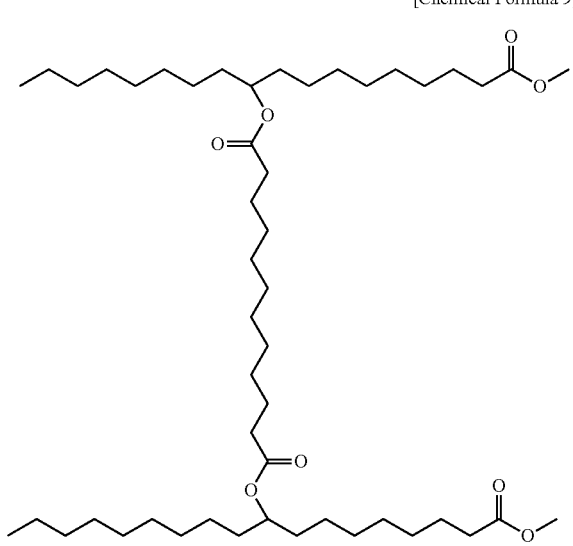
[Chemical Formula 11]
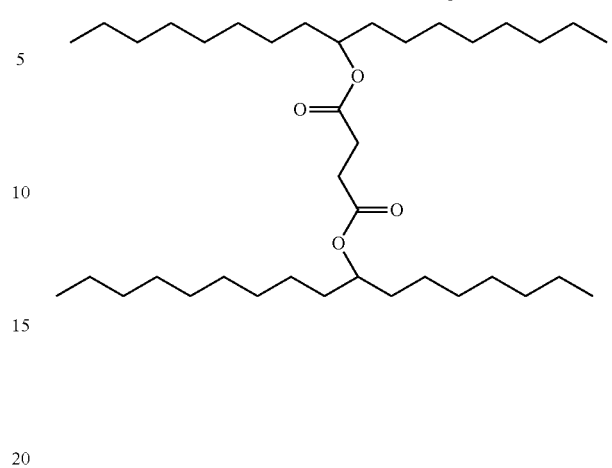
[Chemical Formula 12]
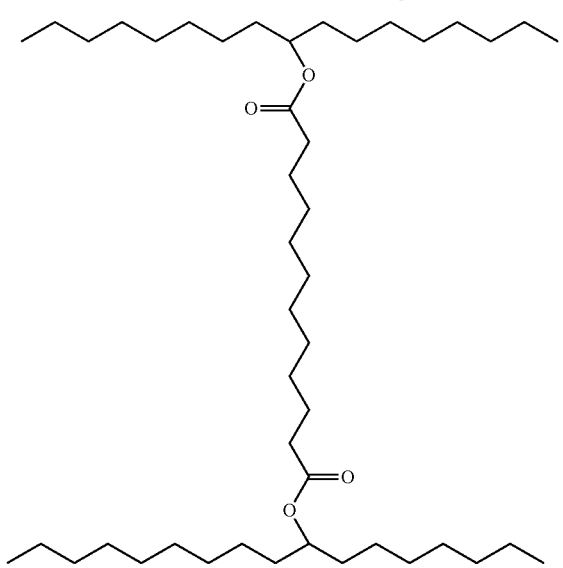
[Chemical Formula 14]
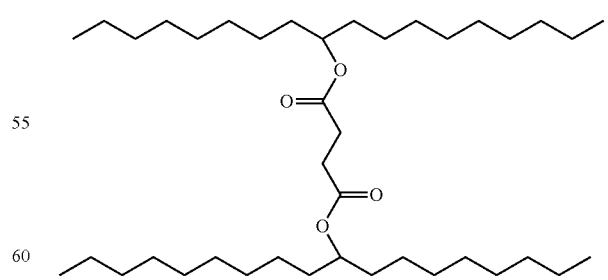

-continued
[Chemical Formula 15]
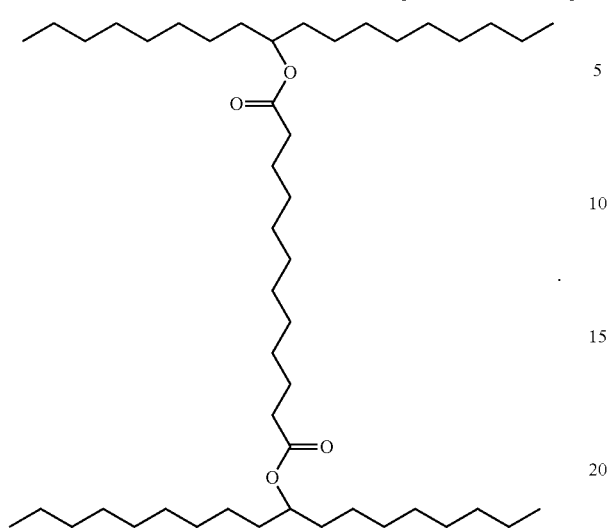
* * * * *